(12) United States Patent
Sutton et al.

(10) Patent No.: US 10,329,228 B1
(45) Date of Patent: Jun. 25, 2019

(54) CONVERSION OF ACETONE AND/OR ALCOHOL(S) TO ALCOHOL(S) AND/OR ALIPHATIC HYDROCARBONS

(71) Applicant: Los Alamos National Security, LLC, Los Alamos, NM (US)

(72) Inventors: Andrew Sutton, Los Alamos, NM (US); Cameron Moore, Los Alamos, NM (US); Rhodri Jenkins, Los Alamos, NM (US); Troy A. Semelsberger, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 15/495,850

(22) Filed: Apr. 24, 2017

Related U.S. Application Data

(60) Provisional application No. 62/327,254, filed on Apr. 25, 2016.

(51) Int. Cl.
*C07C 1/20* (2006.01)
*C07C 45/45* (2006.01)
*C07C 29/145* (2006.01)

(52) U.S. Cl.
CPC .............. *C07C 29/145* (2013.01); *C07C 1/20* (2013.01); *C07C 45/45* (2013.01)

(58) Field of Classification Search
CPC .......... C07C 29/145; C07C 1/20; C07C 45/45
See application file for complete search history.

(56) References Cited

U.S. PATENT DOCUMENTS

| | | | | |
|---|---|---|---|---|
| 5,925,796 A | * | 7/1999 | Bassett | C07C 45/002 568/388 |
| 2008/0293125 A1 | * | 11/2008 | Subbian | C12P 7/04 435/252.3 |
| 2012/0004466 A1 | * | 1/2012 | Martenak | C07C 45/73 568/383 |

FOREIGN PATENT DOCUMENTS

DE 1238453 * 4/1967

OTHER PUBLICATIONS

Alotaibi et al., "Efficient hydrodeoxygenation of biomass-derived ketones over bifunctional Pt-polyoxometalate catalyst," Chem. Commun., 2012, 48, 7194-7196. (Year: 2012).*
English Translation of DE1238453, Apr. 1967, pp. 1-4 (Year: 1967).*
Dileep et al., "Palladium complex in a room temperature ionic liquid: a convenient recyclable reagent for catalytic oxidation," Green Chemistry Letters and Reviews, vol. 7, Issue 1, 2014, pp. 32-36. (Year: 2014).*
Dandekar et al., "Carbon-Supported Copper Catalysts," Journal of Catalysis, 183, 131-154, 1999 (Year: 1999).*
Kozhevnikova, Elena F., et al., "One-step synthesis of methyl isobutyl ketone from acetone catalysed by Pd supported ZnII-CrIII mixed oxide", Journal of Catalysis (2006), 238:286-292.
Ligner, Emanuelle, et al., "Dramatic promotion of cooper-alumina catalysts by sodium for acetone trimerisation", Catal. Sci. Technol. (2014), 4:2480-2483.
Gamman, Jonathan J., et al., "Synthesis of Methyl Isobutyl Ketone over Pd/MgO/SiO2", Ind. Eng. Chem. Res. (2010) 49:8439-8443.

* cited by examiner

*Primary Examiner* — Pancham Bakshi
*Assistant Examiner* — Mark R Luderer
(74) *Attorney, Agent, or Firm* — Lewis Roca Rothgerber Christie LLP

(57) ABSTRACT

A process for the production of saturated or unsaturated aliphatic alcohols and/or hydrocarbons includes condensing acetone and/or alcohol(s) to form one or more carbonyl compounds, and hydrogenating and/or hydrodeoxygenating at least one of the one or more carbonyl compounds to form the saturated or unsaturated alcohol(s) and/or hydrocarbons. In some embodiments, the condensation of acetone and/or alcohol(s) may be carried out in the presence of a solid acid catalyst and a transition metal catalyst. The saturated or unsaturated aliphatic alcohols and/or hydrocarbons may include one or more saturated linear C9 alcohols, C9 alkanes and/or one or more mono-unsaturated C9 alkenes.

20 Claims, 23 Drawing Sheets
(5 of 23 Drawing Sheet(s) Filed in Color)

CONVERSION OF ACETONE AND/OR ALCOHOL(S) TO ALCOHOL(S) AND/OR ALIPHATIC HYDROCARBONS

CROSS-REFERENCE TO RELATED APPLICATION(S)

This application claims priority to and the benefit of U.S. Provisional Application No. 62/327,254, filed Apr. 25, 2016 and titled "CONVERSION OF BIODERIVED ACETONE AND/OR ISOPROPANOL TO ALIPHATIC HYDROCARBONS," the entire content of which is incorporated herein by reference.

STATEMENT REGARDING FEDERALLY SPONSORED RESEARCH OR DEVELOPMENT

The United States government has certain rights in this invention pursuant to Contract No. DE-AC52-06NA25396 between the United States Department of Energy and Los Alamos National Security, LLC for the operation of Los Alamos National Laboratory.

BACKGROUND

Various hydrocarbon compounds are useful as fuel components or fuel additives. These compounds are typically extracted and refined from petroleum, which is a non-renewable fossil fuel. However, the use of petroleum to generate the world's fuel supply has been the subject of much concern for many years, including worries about the depletion of the finite resource and the impact such depletion would have on a world economy that has become dependent on fossil fuel. Additional domestic concerns have centered around the reliance on foreign petroleum stores to meet the country's energy needs. In light of these concerns, some efforts have been undertaken to reduce the world's reliance on fossil fuels and to reduce the country's reliance on foreign petroleum stores. While some of these efforts have made strides in reducing petroleum consumption (e.g., the advent of hybrid and electric vehicles), insufficient progress has been made towards the replacement (or supplementation) of petroleum as the source of the world's fuel needs.

SUMMARY

According to embodiments of the present invention, a process for the production of saturated or unsaturated alcohols (i.e., alcohol product(s) or alcohol reaction product(s)) and/or aliphatic hydrocarbons includes condensing acetone and/or alcohols (i.e., alcohol reactant(s)) (e.g., isopropanol and/or other primary and/or secondary alcohol(s)) to form one or more carbonyl compounds (e.g., one or more aldehydes and/or ketones), and condensing, hydrogenating and/or hydrodeoxygenating at least one of the one or more carbonyl compounds (e.g., aldehydes and/or ketones) to thereby form the saturated or unsaturated alcohols (i.e., alcohol product(s) or alcohol reaction product(s)) and/or aliphatic hydrocarbons. The acetone and/or alcohol condensation may be performed in the presence of first and second catalysts. Additionally, in some embodiments, the alcohol(s) (i.e., alcohol reactant(s)) may be first converted to acetone prior to the condensation reaction. This alcohol conversion reaction may be carried out using the second catalyst described herein for the acetone and/or alcohol condensation reaction.

The first catalyst may include a solid acid or a base, and the second catalyst may include a transition metal catalyst, a zeolite catalyst or a precious metal catalyst. In some embodiments, the first catalyst may include an acidic cation exchange resin. The second catalyst may include a first row transition metal, and in some embodiments the first row transition metal may include Ni, Cu and/or Fe. In some embodiments, the second catalyst may include a precious metal catalyst, and in some embodiments, the precious metal catalyst may include Pt and/or Pd.

In some embodiments, the second catalyst may further include a catalyst support. The catalyst support may include carbon, alumina and/or silica.

In some embodiments, the condensation, hydrogenation and/or hydrodeoxygenation of the one or more carbonyl compounds (e.g., aldehydes and/or ketones) includes first hydrogenating the one or more carbonyl compounds (i.e., converting the carbonyl compound to an alcohol), and then hydrodeoxygenating the resulting alcohol (i.e., converting the alcohol to a saturated hydrocarbon). According to some embodiments, however, the condensation, hydrogenation and/or hydrodeoxygenation of the one or more carbonyl compounds is performed in a single process in which hydrogenation (to the alcohol) and hydrodeoxygenation (to the saturated hydrocarbon) occur simultaneously (e.g., in a one-pot process) to form the one or more saturated hydrocarbons. Additionally, in some embodiments, the process may cease after hydrogenation of the carbonyl compound(s), yielding the alcohol(s) (i.e., the alcohol product(s) or alcohol reaction product(s)).

According to some embodiments, the one or more carbonyl compounds (e.g., one or more aldehydes and/or ketones) resulting from the condensation of acetone and/or alcohol(s) (i.e., alcohol reactant(s)) may include one or more C6, C9 or C12 carbonyl compounds (e.g., aldehydes and/or ketones). For example, in some embodiments, the condensation of acetone and/or alcohol reactant(s) (e.g., isopropanol and/or other primary and/or secondary alcohol(s)) results in the production of a mixture of at least two carbonyl compounds (e.g., two aldehydes and/or ketones), for example 4 carbonyl compounds (e.g. aldehydes and/or ketones). The one or more carbonyl compounds (e.g. aldehydes and/or ketones) may be aliphatic or linear. In some embodiments, for example, the condensation of acetone and/or isopropanol results in a mixture of 4-methyl-2-pentanone, 2,6-dimethyl-4-heptanone, 4,6-dimethyl-2-heptanone, and 2,6,8-trimethyl-4-nonanone in varying yields, which yields are adjustable by tuning different reaction parameters. For example, in some embodiments, the condensation reaction may yield up to 36% carbon yield of 4-methyl-2-pentanone, up to 24% carbon yield of 2,6-dimethyl-4-heptanone, up to 6% carbon yield of 4,6-dimethyl-2-heptanone, and up to 34% carbon yield of 2,6,8-trimethyl-4-nonanone.

The one or more carbonyl compounds (e.g. aldehydes and/or ketones) are then condensed, hydrogenated and/or hydrodeoxygenated to form one or more saturated or unsaturated alcohols (i.e., alcohol product(s) or alcohol reaction product(s)) and/or aliphatic hydrocarbons. For example, in some embodiments, the one or more carbonyl compounds (e.g. aldehydes and/or ketones) may be first hydrogenated to form one or more alcohols, and then hydrodeoxygenated to form the one or more saturated or unsaturated aliphatic hydrocarbons. In some embodiments, the process may cease after hydrogenation to the alcohol(s) (i.e., the alcohol product(s) or alcohol reaction product(s)). In some embodiments, the hydrogenation of the one or more carbonyl compounds (e.g. aldehydes and/or ketones) may be carried out in the presence of the second catalyst (i.e., the second catalyst described herein with respect to the condensation of acetone and/or alcohol reactant(s)) and the hydrodeoxygenation of the resulting one or more alcohols may be carried out in the presence of the first catalyst (i.e., the first catalyst described herein with respect to the condensation of acetone and/or alcohol reactant(s)). In some embodiments, hydrogenation and hydrodeoxygenation of the one or more carbonyl compounds (e.g. aldehydes and/or ketones) may be performed in a one-pot process in which the one or more carbonyl compounds (e.g. aldehydes and/or ketones) are processed in the presence of both the first and second catalysts. The hydrogenation and/or hydrodeoxygenation reactions (whether step-wise or one-pot) may be tailored to produce either saturated or unsaturated alcohol(s) (i.e., alcohol product(s) or alcohol reaction product(s)) and/or hydrocarbons, and to produce varying yields of the resulting alcohol(s) (i.e., alcohol product(s) or alcohol reaction product(s)) and/or hydrocarbons.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features of embodiments of the present invention can be better understood by reference to the following detailed description when considered in conjunction with the following drawings in which:

in FIG. 12A, 150° C. in FIG. 12B, and 190° C. in FIG. 12C). In the graphs, A-15 is Amberlyst 15, and A-36 is Amberlyst 36. In FIG. 12A, A-15 is shown as an aquamarine trace, A-36 is shown as a yellow trace, HZSM is shown as an orange trace, $ZrO_2$ is shown as a gray trace, $Al_2O_3$ is shown as a blue trace, and Nafion is shown as a green trace. In FIG. 12B, H-ZSM-5 is shown as an aquamarine trace, Nafion is shown as an orange trace, and A-36 is shown as a gray trace. Finally, in FIG. 12C, Nafion is shown as a blue trace, and HZSM-5 is shown as a red trace.

DETAILED DESCRIPTION

Figure 1:
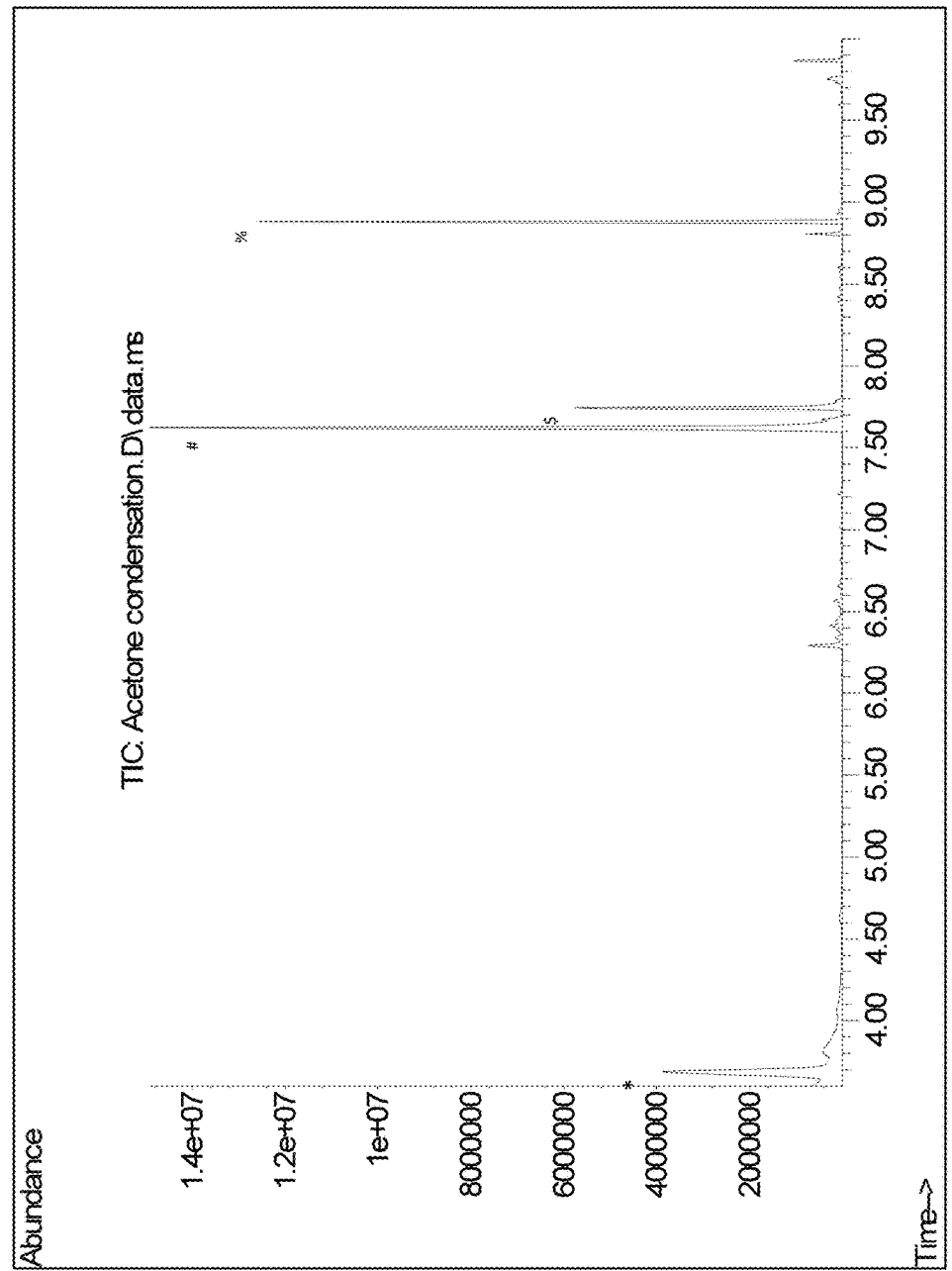
FIG. 1 is a GC-MS spectrum of the reaction product achieved from the process of Condensation Example 1, in which the peak for 4-methyl-2-pentanone is denoted *, the peak for 2,6-dimethyl-4-heptanone is denoted #, the peak for 4,6-dimethyl-2-heptanone is denoted $, and the peak for 2,6,8-trimethyl-4-nonane is denoted %.

According to embodiments of the present invention, a process for the conversion of acetone and/or alcohols (i.e., alcohol reactants) to saturated alcohol(s) (i.e., alcohol product(s) or alcohol reaction product(s), e.g., chain extended alcohol(s)) and/or hydrocarbons includes the condensation of acetone and/or alcohol reactant(s) to yield one or more carbonyl compounds (e.g. aldehydes and/or ketones), and the condensation, hydrogenation and/or hydrodeoxygenation of the one or more carbonyl compounds (e.g. aldehydes and/or ketones) to yield one or more saturated alcohols (i.e., alcohol products or alcohol reaction products) and/or hydrocarbons. As used herein, the term "carbonyl compounds" and similar terms refer to compounds containing at least one carbonyl group, and indicate the carbonyl-containing compounds resulting from the condensation of the acetone and/or alcohol reactant(s). For example, in some embodiments, for example, the condensation of acetone and/or certain alcohols (e.g., isopropanol or other secondary alcohols) results in one or more ketones as the carbonyl compound(s). According to some embodiments, however, the condensation of certain alcohols (e.g., primary alcohols) results in one or more aldehydes as the carbonyl compounds.

In some embodiments, the condensation, hydrogenation and/or hydrodeoxygenation of the one or more carbonyl compounds (e.g. aldehydes and/or ketones) includes a stepwise reaction scheme in which the one or more carbonyl compounds (e.g. aldehydes and/or ketones) is first hydrogenated (converting the ketone to an alcohol), and then hydrodeoxygenated (converting the alcohol to a saturated hydrocarbon). According to some embodiments, however, the condensation, hydrogenation and/or hydrodeoxygenation of the one or more carbonyl compounds (e.g. aldehydes and/or ketones) includes a one-pot process in which hydrogenation and hydrodeoxygenation occur simultaneously to form the one or more saturated hydrocarbons. In some embodiments, the process may cease after hydrogenation of the ketones to form the alcohol(s) (i.e., the alcohol product(s) or alcohol reaction product(s)), which resulting alcohol(s) may be useful in their own right as fuel additives.

Any suitable acetone and/or alcohol (i.e., alcohol reactant) starting material may be used, including synthetic acetone, bioderived acetone, and any alcohol. As used herein, the term "synthetic acetone" refers to acetone produced by any known synthetic route, including, but not limited to the cumene process (i.e., alkylation of benzene with propylene followed by oxidation to acetone and phenol), the Wacker-Hoechst process (i.e., direct oxidation of propylene), or the hydration and oxidation of propylene. Additionally, as used herein, the term "bioderived acetone" refers to acetone derived from a bio-mass. For example, the acetone may be produced from sugars obtained from various bio-mass sources, including, e.g., corn, etc. Also, many commercially available bioderived acetone products include a mixture of acetone and alcohol (e.g., isopropanol or other primary or secondary alcohol). As discussed herein, alcohols (i.e., alcohol reactants) and/or acetone may be converted to the one or more carbonyl compounds (e.g. aldehydes and/or ketones) and the one or more saturated alcohols (i.e., alcohol products or alcohol reaction products, e.g., chain extended alcohols) and/or hydrocarbons by the same chemical processes. As such, any reference herein to "acetone," "alcohol" or "isopropanol" (i.e., alcohol reactant) is intended to encompass acetone, any alcohol (including isopropanol and any other primary and/or secondary alcohol(s)), as well as mixtures of such compounds.

As discussed above, according to embodiments of the present invention, the process for conversion of acetone and/or alcohol(s) (i.e., alcohol reactant(s), e.g., isopropanol or other primary and/or secondary alcohol(s)) to one or more saturated alcohols (i.e., alcohol product(s) or alcohol reaction product(s)) and/or hydrocarbons includes the condensation of acetone and/or alcohol(s) (i.e., alcohol reactant(s), e.g., isopropanol or other primary and/or secondary alcohol(s)) to yield one or more carbonyl compounds (e.g. aldehydes and/or ketones) which are then further processed. In this initial condensation of acetone and/or alcohols (i.e., alcohol reactants, e.g., isopropanol or other primary and/or secondary alcohol(s)), in some embodiments, the reaction may be carried out using first and second catalysts. The first catalyst may be a solid acid catalyst or a basic catalyst. Any suitable basic catalyst may be used, many of which are known to those skilled in the art, and a nonlimiting example of which is aqueous NaOH. Any suitable solid acid catalyst may be used as the first catalyst, nonlimiting examples of which include acidic cation exchanges resins, including, for example those with sulfonic acid functional groups, such as the NAFION line of products available from The Chemours Company FC, LLC, which is an affiliate of E. I. DuPont de Nemours and Company (NAFION is a registered trademark of The Chemours Company FC, LLC, Wilmington, Del.), and the AMBERLYST line of products available from various suppliers, including The Dow Chemical Company, Sigma Aldrich Co. LLC and Rohm & Haas Company (AMBERLYST is a registered trademark of Rohm & Haas Company, Philadelphia, Pa.). In some embodiments, the first catalyst includes AMBERLYST 15 and/or AMBERLYST 36 (available from The Dow Chemical Company, Sigma Aldrich Co. LLC or Rohm & Haas Company), and/or NAFION (available from The Chemours Company FC, LLC).

The second catalyst may be a transition metal catalyst, zeolite catalyst, or precious metal catalyst, and may (but does not necessarily) include a catalyst support. Any suitable transition metal may be used as the transition metal catalyst. Indeed, in some embodiments, the transition metal may include any metal or combination of metals from Groups 3 through 12 on the periodic chart. In some embodiments, the transition metal includes a first-row transition metal, i.e., Sc, Ti, V, Cr, Mn, Fe, Co, Ni, Cu and/or Zn. According to some embodiments, the transition metal may include Ni, Cu or Fe. Additionally, in some embodiments, the transition metal (or combination of transition metals) may be used in elemental or metal form as the catalyst, or may be used in oxide form.

According to some embodiments, the second catalyst may include a zeolite catalyst. Any suitable zeolite catalyst may be used as the second catalyst. Some nonlimiting examples of suitable zeolite catalysts include ZSM-5 series zeolites, such as, for example, HZSM-5 (also referred to herein interchangeably as H-ZSM-5, H-ZSM5 or HZSM5). In some embodiments, the zeolite catalyst may include a transition metal impregnated or ion-exchanged zeolite. The transition metal in these impregnated or ion-exchanged zeolites may be any suitable transition metal, including, for example, any metal or combination of metals from Groups 3 through 12 on the periodic chart. In some embodiments, the transition metal may include a first-row transition metal, i.e., Sc, Ti, V, Cr, Mn, Fe, Co, Ni, Cu and/or Zn. According to some embodiments, the transition metal may include Ni, Cu or Fe.

In some embodiments, the second catalyst may include a precious metal catalyst. Any suitable precious metal may be used in the precious metal catalyst, including Au, Ag, Pt and/or Pd. In some embodiments, the precious metal catalyst may include Pt and/or Pd.

Conventional wisdom dictates that Pt and Pd (or other precious metal catalysts) would provide the best catalytic activity and provide the best reaction kinetics and yield. However, it has been surprisingly found that the use of transition metal catalysts in the processes according to embodiments of the present invention lead to significantly improved reaction kinetics and product yield as compared to the precious metal catalysts. Indeed, in some embodiments, the use of Ni, Cu and/or Fe catalysts with or without a catalyst support produced better reaction kinetics and product yield than a Pd-on-carbon support. As precious metals are significantly more expensive than transition metals, this surprising result drastically reduces the cost of producing the one or more saturated hydrocarbons.

As noted above, the second catalyst may include, but does not necessarily include a catalyst support. When a catalyst support is present, any suitable catalyst support may be used. Some non-limiting examples of suitable catalyst supports include carbon, alumina and silica. A single catalyst support material may be used, or a combination of materials may be used. For example, in some embodiments, the catalyst support may include a complex oxide of both alumina and silica (e.g., $SiO_2$—$Al_2O_3$ or $Al_2O_3$—$AlO_2$). Additionally, when a catalyst support is used, the second catalyst can be combined with any suitable catalyst support, without limitation. Nonlimiting examples, of suitable catalyst/catalyst support combinations include $Ni/SiO_2$—$Al_2O_3$, $Pd/Al_2O_3$, Pd/C, Ni/C, and $CuO/Al_2O_3$. In some embodiments, for example the second catalyst may include $Ni/SiO_2$—$Al_2O_3$ and/or $CuO/Al_2O_3$.

Prior to condensation of the acetone and/or alcohol(s) (i.e., alcohol reactant(s)) to carbonyl compounds (e.g. aldehydes and/or ketones), as discussed above, the alcohol(s) (i.e., the alcohol reactant(s), e.g., isopropanol and/or other primary and/or secondary alcohol(s)) may be first converted to acetone. Such an initial reaction of the alcohol reactant(s) can provide hydrogen gas for the initial condensation reaction of the acetone and/or alcohol reactant(s) to produce the carbonyl compounds (e.g. aldehydes and/or ketones). This initial reaction of the alcohol reactant(s) can be carried out using the second catalyst described herein in connection with the initial condensation reaction of the acetone and/or alcohol reactant(s).

The condensation of acetone and/or alcohol(s) (i.e., alcohol reactant(s)) may also be carried out in the presence of a suitable solvent. Any suitable organic solvent can be used, nonlimiting examples of which include cyclohexane, hexadecane, short-chain alcohols (such as, e.g., methanol and ethanol), linear and branched hydrocarbons, and linear and branched cyclic ethers.

The condensation reaction may be carried out under any conditions suitable to progress the reaction toward the production of the one or more carbonyl compounds (e.g. aldehydes and/or ketones). For example, the reaction may be carried out under any suitable heat and pressure conditions. In some embodiments, for example, a reaction vessel including a reaction mixture of the acetone and/or isopropanol, the first and second catalysts and the solvent may be flushed with a mixture of $H_2$ and an inert gas (e.g., Ar or $N_2$) and then pressurized to a suitable pressure (e.g., 150 to 350 psig, or 200 to 300 psig). The reaction vessel may then be heated to a suitable temperature to drive the reaction. According to embodiments of the present invention, the reaction temperature may be relatively low, e.g., about 80° C. to about 200° C. The vessel may be subjected to these conditions for any suitable amount of time to complete the reaction. For example, in some embodiments, the reaction time may be about 10 hours to about 30 hours, or about 14 hours to about 24 hours.

Condensation of acetone and/or alcohols (i.e., alcohol reactants) according to embodiments of the present invention results in the production of one or more carbonyl compounds (e.g. aldehydes and/or ketones). The one or more carbonyl compounds (e.g. aldehydes and/or ketones) may include one or more C6, C9 or C12 carbonyl compounds (e.g. aldehydes and/or ketones). In some embodiments, the condensation of acetone and/or isopropanol results in the production of a mixture of at least two carbonyl compounds (e.g. aldehydes and/or ketones), for example 4 carbonyl compounds (e.g. aldehydes and/or ketones). In some embodiments, the one or more carbonyl compounds (e.g. aldehydes and/or ketones) resulting from the condensation of acetone and/or isopropanol includes a mixture of at least two of a C6 carbonyl compound (e.g. aldehyde or ketone), a C9 carbonyl compound (e.g. aldehyde or ketone) and a C12 carbonyl compound (e.g. aldehyde or ketone). Additionally, in some embodiments the one or more carbonyl compounds (e.g. aldehydes and/or ketones) (for example the C6 carbonyl compound, C9 carbonyl compound and/or C12 carbonyl compound) are aliphatic or linear. In some embodiments, the one or more carbonyl compounds (e.g. aldehydes and/or ketones) include at least one C6 carbonyl compound, at least one C9 carbonyl compound, and at least one C12 carbonyl compound. In some embodiments, the one or more carbonyl compounds (e.g. aldehydes and/or ketones) include a mixture of a C6 carbonyl compound, two C9 carbonyl compounds, and a C12 carbonyl compound. In some embodiments, the C6 carbonyl compound includes 4-methyl-2-pentanone, the C9 carbonyl compound includes 2,6-dimethyl-4-heptanone and/or 4,6-dimethyl-2-heptanone, and the C12 carbonyl compound may include 2,6,8-trimethyl-4-nonanone. In some embodiments, for example, the condensation of acetone and/or alcohols (i.e., alcohol reactants) results in a mixture of 4-methyl-2-pentanone, 2,6-dimethyl-4-heptanone, 4,6-dimethyl-2-heptanone, and 2,6,8-trimethyl-4-nonanone in varying yields.

As discussed above, according to embodiments of the present invention, the condensation of acetone and/or alcohols (i.e., alcohol reactants) results in a mixture of 4-methyl-2-pentanone, 2,6-dimethyl-4-heptanone, 4,6-dimethyl-2-heptanone, and 2,6,8-trimethyl-4-nonanone in varying yields. For example, in some embodiments, the condensation reaction may yield up to 36% carbon yield of 4-methyl-2-pentanone, up to 24% carbon yield of 2,6-dimethyl-4-heptanone, up to 6% carbon yield of 4,6-dimethyl-2-heptanone, and up to 34% carbon yield of 2,6,8-trimethyl-4-nonanone. The yield of the individual carbonyl compounds may be adjusted by tuning certain reaction parameters. For example, the ratios of yield of the four different carbonyl compounds may be altered by adjusting the type and/or amount of catalyst, the reaction temperature, the reaction time, or the reaction pressure. Additionally, while the condensation of acetone yields the same carbonyl compounds (e.g., ketones) as the condensation of isopropanol, the condensation of isopropanol yields the carbonyl compounds in different ratios than the condensation of acetone. Accordingly, the ratios of yield of the four different carbonyl compounds may be further tuned by adding isopropanol (or other alcohol reactant(s)) to the acetone starting material, and/or by adjusting the amount of isopropanol (or other alcohol reactant(s)) in the acetone/alcohol mixture.

CONDENSATION EXAMPLES

The following condensation examples are provided for illustrative purposes only, and do not limit the scope of the embodiments of the present invention.

Materials and Methods

All chemicals and reagent grade solvents were obtained from commercial vendors and were used as received. $^1H$ and $^{13}C$ NMR spectra were obtained at room temperature on a Bruker AV400 MHz spectrometer, with chemical shifts (d) referenced to the residual solvent signal ($^1H$ and $^{13}C$). GC-MS analysis was carried out using a Hewlett-Packard 6890 GC system equipped with a Hewlett-Packard 5973 mass selective detector.

Condensation Example 1—Condensation of Acetone (and/or Alcohol Reactant(s), Such as Isopropanol)

As depicted in the below Reaction Scheme 1, acetone (0.20 mL; 2.72 mmol) was added to a mixture of Amberlyst 15 (0.20 g; obtained from Sigma-Aldrich Co. LLC) and Ni/SiO$_2$—Al$_2$O$_3$ (0.018 g; 65 wt % Ni, 0.20 mmol) in a stainless steel tube reactor containing a Teflon-lined stir bar. Cyclohexane (3 mL) was added and the tube was sealed, flushed with Ar/H$_2$ (94:6) then pressurized to 250 psig. The tube was heated to 120° C. and stirred at 500 rpm. After 24 hours, the tube was cooled in a water bath and the mixture was analyzed by GCMS (shown in FIG. 1) and $^1H$ NMR.

Reaction Scheme 1

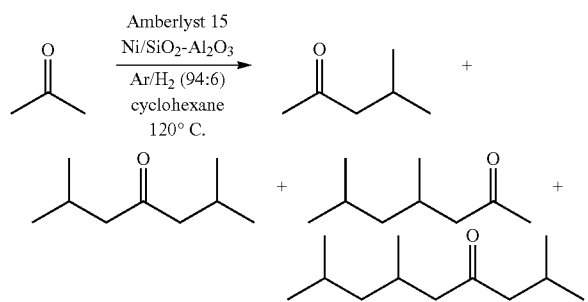

Condensation Example 2—Condensation of Acetone (and/or Alcohol Reactant(s), Such as Isopropanol)

Acetone condensation was carried out in a manner similar to that described above in connection with Condensation Example 1, except that Pd/C was used as the second catalyst instead of Ni/SiO$_2$—Al$_2$O$_3$. In particular, acetone (0.20 mL; 2.72 mmol) was added to a mixture of Amberlyst 15 (0.20 g) and Pd/C (0.008 g; 10 wt % Pd, 0.003 mmol) in a stainless steel tube reactor containing a Teflon-lined stir bar. Cyclohexane (3 mL) was added and the tube was sealed, flushed with Ar/H$_2$ (94:6) then pressurized to 250 psig. The tube was heated to 120° C. and stirred at 500 rpm. After 14 hours, the tube was cooled in a water bath and the mixture was analyzed by GCMS and $^1$H NMR.

4-Methyl-2-pentanone (up to 36% carbon yield), 2,6-dimethyl-4-heptanone (up to 24%), 4,6-dimethyl-2-heptanone (up to 6%) and 2,6,8-trimethyl-4-nonane (up to 34%) were observed as major products of the acetone condensation; with the ratios dependent on the catalyst, reaction temperature, reaction time and pressure.

After condensation of the acetone and/or isopropanol, the one or more carbonyl compounds (e.g. aldehydes and/or ketones) may include a mixture of carbonyl compounds (e.g. aldehydes and/or ketones), as discussed above. When the one or more carbonyl compounds (e.g. aldehydes and/or ketones) includes a mixture of carbonyl compounds, for example, a mixture of 4-methyl-2-pentanone, 2,6-dimethyl-4-heptanone, 4,6-dimethyl-2-heptanone, and 2,6,8-trimethyl-4-nonanone, the process according to embodiments of the present invention may include separation of the carbonyl compounds before further processing. The separation may be accomplished by any suitable separation technique, which techniques are known to those skilled in the art (e.g., high-performance liquid chromatography, etc.).

After separation, the 4-methyl-2-pentanone (also known as methyl isobutyl ketone, or MIBK) and the 2,6,8-trimethyl-4-nonanone need not be subjected to further reaction or processing. Instead, these compounds can be used in their carbonyl forms (e.g., aldehyde or ketone forms) as fuel additives. Indeed, as the 2-methylpentane product expected from the hydrodeoxygenation of MIBK is not a desirable fuel additive or component, hydrodeoxygenation of MIBK is neither necessary nor desirable for the production of hydrocarbon fuel components.

However, if desired, the MIBK can be further condensed to produce longer carbon chain ketones, which can be useful as fuel additives. For example, in some embodiments, the MIBK may be condensed under similar condensation reaction conditions and using similar reactants as those described above in connection with the condensation of acetone. Condensation of MIBK in this manner yields an additional amount of 2,6,8-trimethyl-4-nonanone (i.e., additional to the amount of this compound produced during the condensation of the acetone and/or alcohol reactant), a C12 ketone that is also useful as a fuel additive. The following Condensation Examples 3 and 4 describe representative (but not limiting) reaction schemes for this conversion.

Condensation Example 3—Condensation of MIBK

Figure 2:
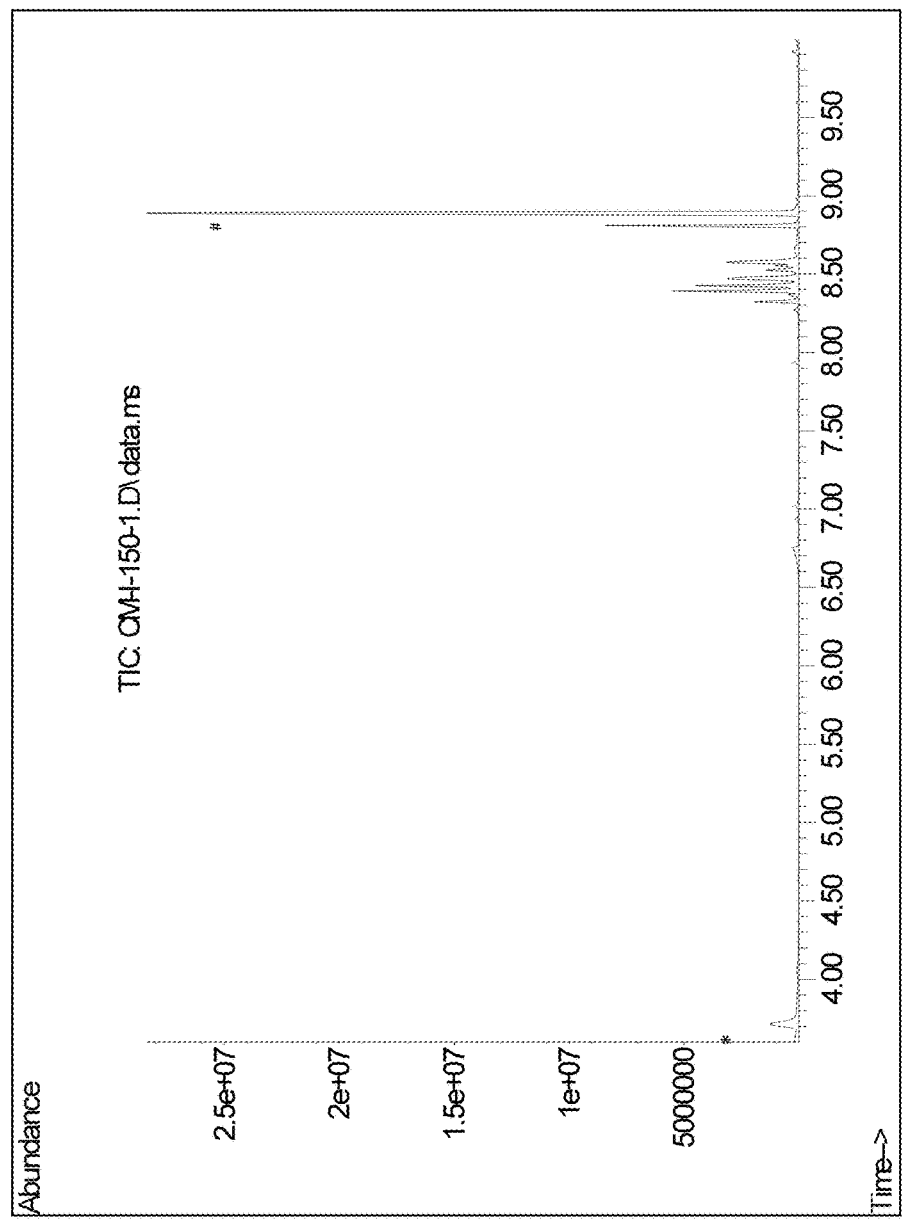
FIG. 2 is a GC-MS spectrum of the reaction product achieved from the process of Condensation Example 3, in which the peak for unreacted MIBK is denoted *, and the peak for 2,6,8-trimethyl-4-nonane is denoted #.

As depicted in the below Reaction Scheme 2, 4-Methyl-2-pentanone (340 µL; 2.72 mmol) was added to a mixture of Amberlyst 15 (0.20 g) and Ni/SiO$_2$—Al$_2$O$_3$ (0.038 g; 65 wt % Ni, 0.42 mmol) in a stainless steel tube reactor containing a Teflon-lined stir bar. Cyclohexane (3 mL) was added and the tube was sealed, flushed with Ar/H$_2$ (94:6), and then pressurized to 250 psig. The tube was heated to 100° C. and stirred at 500 rpm. After 24 hours, the tube was cooled in a water bath and the mixture was analyzed by GCMS (shown in FIG. 2) and $^1$H NMR.

Reaction Scheme 2

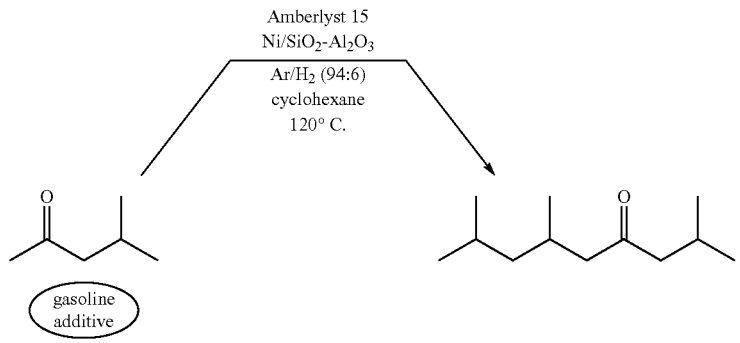

Condensation Example 4—Condensation of MIBK

MIBK condensation was carried out in a manner similar to that described above in connection with Condensation Example 3, except that Pd/C was used as the second catalyst instead of Ni/SiO$_2$—Al$_2$O$_3$. In particular, 4-Methyl-2-pentanone (340 µL; 2.72 mmol) was added to a mixture of Amberlyst 15 (0.20 g) and Pd/C (0.008 g; 10 wt % Pd, 0.003 mmol) in a stainless steel tube reactor containing a Teflon-lined stir bar. Cyclohexane (3 mL) was added and the tube was sealed, flushed with Ar/H$_2$ (94:6), and then pressurized to 250 psig. The tube was heated to 120° C. and stirred at 500 rpm. After 14 hours, the tube was cooled in a water bath and the mixture was analyzed by GCMS and $^1$H NMR.

2,6,8-trimethyl-4-nonanone (up to 41% carbon yield; depending on the catalyst, reaction temperature, reaction time and pressure) was observed as the major product of the 4-methyl-2-pentanone (MIBK) condensation.

The remaining carbonyl compounds (e.g., ketones) produced by the acetone (and/or alcohol reactant(s), such as, isopropanol) condensation (i.e., 2,6-dimethyl-4-heptanone and 4,6-dimethyl-2-heptanone) may be further processed to yield the one or more saturated alcohol(s) (i.e., alcohol product(s) or alcohol reaction product(s)) and/or hydrocarbons. In some embodiments, for example, these C9 carbonyl compounds (e.g. aldehydes and/or ketones) can be hydrogenated and hydrodeoxygenated to form one or more C9 saturated alkanes. According to some embodiments, the C9 carbonyl compounds (e.g. aldehydes and/or ketones) may be hydrogenated to form corresponding alcohols (e.g., 2,6-dimethyl-4-heptanol and/or 4,6-dimethyl-2-heptanol). The process may cease at this point, and the resulting C9 alcohols (i.e., alcohol products) may be used in their own right. In some embodiments, however, the resulting C9 alcohols may serve as intermediate alcohols which may be subsequently hydrodeoxygenated to form the C9 saturated alkanes (e.g., 2,6-dimethyl-4-heptane and/or 4,6-dimethyl-2-heptane). Additionally, in some embodiments, the C9 carbonyl compounds (e.g. aldehydes and/or ketones) may be hydrogenated and hydrodeoxygenated in a one-pot process to yield the C9 saturated alkanes.

The C9 carbonyl compounds (i.e., 2,6-dimethyl-4-heptanone (i.e., diisobutyl ketone or DIBK) and 4,6-dimethyl-2-heptanone produced by the acetone (and/or alcohol reactant(s)) condensation may be hydrogenated separately or together. Hydrogenation of the C9 carbonyl compounds (either separately or together) can be carried out in a manner similar to that described above for the condensation of acetone and/or alcohol reactant(s) but omitting the first catalyst (i.e., the solid acid, or basic catalyst). In particular, the hydrogenation of the C9 carbonyl compounds (e.g. aldehydes and/or ketones) may occur in the presence of the second catalyst (described above in connection with the condensation of acetone and/or isopropanol) and H$_2$ gas. The hydrogenation reaction may be carried out under any conditions suitable to progress the reaction toward the production of the relevant corresponding alcohol. For example, the reaction may be carried out under any suitable heat and pressure conditions. In some embodiments, for example, a reaction vessel including a reaction mixture of the C9 carbonyl compounds (e.g. aldehydes and/or ketones), and the second catalyst may be purged with H$_2$ and then pressurized to a suitable pressure (e.g., 100 to 350 psig, or 200 to 300 psig). The reaction vessel may then be heated to a suitable temperature to drive the reaction. According to embodiments of the present invention, the reaction temperature may be relatively low, e.g., about 80° C. to about 200° C., or about 100° C. to about 150° C. The vessel may be subjected to these conditions for any suitable amount of time to complete the reaction. For example, in some embodiments, the reaction time may be about 10 hours to about 30 hours, or about 14 hours to about 24 hours.

According to some embodiments, the alcohol produced from the hydrogenation of the C9 carbonyl compounds (e.g. aldehydes and/or ketones) may be hydrodeoxygenated to yield C9 saturated alkanes, which are useful as fuel components, e.g., diesel fuel components. In some embodiments, the alcohol produced from the hydrogenation of the C9 carbonyl compounds (e.g. aldehydes and/or ketones) may be hydrodeoxygenated to yield C9 mono-unsaturated alkenes, which are useful in various industries as, e.g., surfactants. As the hydrodeoxygenation reaction of the C9 carbonyl compounds (e.g. aldehydes and/or ketones) first converts the alcohol to the corresponding mono-unsaturated alkene, and then converts the alkene to the alkane, the hydrodeoxygenation reaction can be carried out in the same manner as described below for the conversion to alkanes, but can be tailored to yield the alkenes by adjusting the reaction time. For example, in some embodiments, to tailor the hydrodeoxygenation reaction to yield alkenes rather than alkanes, the reaction may be carried out for a shorter period of time than that needed to complete the conversion all the way to the alkanes. In some embodiments, for example, to yield alkenes (rather than alkanes) the reaction can be carried out for 2 minutes to 2 hours, for example, 5 minutes to 70 minutes, or 10 minutes to 60 minutes. Alternatively, in some embodiments, the hydrodeoxygenation reaction may be carried out in the absence of H$_2$, thereby forcing the reaction to stop after alkene synthesis, and providing no reaction pathway for alkane synthesis.

As discussed above, the process according to some embodiments may cease (or be completed) after synthesis of the alcohols (i.e., the alcohol products or alcohol reaction products, e.g., the chain extended C9 alcohols). However, in some embodiments, the process may continue, and the C9 alcohols (i.e., 2,6-dimethyl-4-heptanol and/or 4,6-dimethyl-2-heptanol) produced by the hydrogenation of the C9 carbonyl compounds (e.g. aldehydes and/or ketones) may serve as intermediate alcohols that may be hydrodeoxygenated. The C9 alcohols may be hydrodeoxygenated either separately or together. Hydrodeoxygenation of the C9 alcohols (either separately or together) can be carried out in a manner similar to that described above for the condensation of acetone and/or isopropanol but omitting the second catalyst (i.e., the transition metal, precious metal or zeolite catalyst). In particular, the hydrodeoxygenation of the C9 alcohols may occur in the presence of the first catalyst (described above in connection with the condensation of acetone and/or isopropanol) and H$_2$ gas. The hydrodeoxygenation reaction may be carried out under any conditions suitable to progress the reaction toward the production of the relevant corresponding alkenes and/or alkanes. For example, the reaction may be carried out under any suitable heat and pressure conditions. In some embodiments, for example, a reaction vessel including a reaction mixture of the C9 alcohols, and the first catalyst may be purged with H$_2$ and then pressurized to a suitable pressure (e.g., 100 to 350 psig, or 200 to 300 psig). In some embodiments, the same vessel used for the above described hydrogenation reaction may be used, in which case, the vessel need not be purged, and may instead be pressurized to the appropriate pressure. The reaction vessel may then be heated to a suitable temperature to drive the reaction. According to embodiments of the present invention, the reaction temperature may be relatively low, e.g., about 80° C. to about 200° C., or about 100° C. to about 150° C. The vessel may be subjected to these conditions for any suitable amount of time to complete the reaction. For example, in some embodiments, the reaction time may be about 1 hour to about 5 hours, or about 1 hour to about 3 hours.

HYDROGENATION AND HYDRODEOXYGENATION EXAMPLES

The following hydrogenation and hydrodeoxygenation examples are provided for illustrative purposes only, and do not limit the scope of the embodiments of the present invention.

Hydrogenation Example 1—Hydrogenation of 2,6-dimethyl-4-heptanone

Diisobutyl ketone (4.0 mL; 22.7 mmol) and Ni/SiO$_2$—Al$_2$O$_3$ (0.20 g; 65 wt % Ni, 2.22 mmol) were loaded into a 50 mL stainless steel bomb reactor fitted with an overhead stirring device. The reactor was purged with H$_2$ and then pressurized to 200 psig and heated to 150° C. with stirring at 300 rpm. After about 20 hours, the reactor was cooled and slowly vented. GC-MS analysis of an aliquot of the reaction mixture revealed about 70% conversion to 2,6-dimethyl-4-heptanol.

Hydrogenation Example 2—Hydrogenation of 2,6-dimethyl-4-heptanone 2,6-dimethyl-4-heptanone was hydrogenated in a manner similar to that described in Hydrogenation Example 1, except that CuO/Al$_2$O$_3$ was used instead of Ni/SiO$_2$—Al$_2$O$_3$. In particular, diisobutyl ketone (4.0 mL; 22.7 mmol) and CuO/Al$_2$O$_3$ (1.00 g; 13 wt % Cu, 1.63 mmol) were loaded into a 50 mL stainless steel bomb reactor fitted with an overhead stirring device. The reactor was purged with H$_2$ and then pressurized to 200 psig and heated to 150° C. with stirring at 300 rpm. After about 20 hours, the reactor was cooled and slowly vented. GC-MS analysis of an aliquot of the reaction mixture revealed about 70% conversion to 2,6-dimethyl-4-heptanol.

Hydrodeoxygenation Example 1—Hydrodeoxygenation of 2,6-dimethyl-4-heptanone

Hydrogenation:
Diisobutyl ketone (4.0 mL; 22.7 mmol) and Ni/SiO$_2$—Al$_2$O$_3$ (0.20 g; 65 wt % Ni, 2.22 mmol) were loaded into a 50 mL stainless steel bomb reactor fitted with an overhead stirring device. The reactor was purged with H$_2$ and then pressurized to 200 psig and heated to 150° C. with stirring at 300 rpm. After about 20 hours, the reactor was cooled and slowly vented. GC-MS analysis of an aliquot of the reaction mixture revealed about 70% conversion to 2,6-dimethyl-4-heptanol.

Hydrodeoxyqenation:
Amberlyst 15 (0.5 g) was added to the mixture and the reactor was pressurized to 200 psig H$_2$ and heated to 120° C. After 2 hours, the reactor was cooled and vented. GC-MS analysis of an aliquot of the reaction mixture revealed near quantitative conversion to 2,6-dimethylheptane.

As discussed above, the C9 carbonyl compounds (e.g. aldehydes and/or ketones) may be hydrogenated and/or hydrodeoxygenated in a one-pot process to yield the C9 saturated alcohols, alkenes and/or alkanes that are useful in various fuel applications, e.g., gasoline, diesel and jet fuel applications. In some embodiments, the one-pot hydrodeoxygenation of the C9 carbonyl compounds (either separately or together) can be carried out in a manner similar to that described above for the condensation of acetone and/or alcohol reactant(s) but maintaining a constant H$_2$ pressure throughout the reaction. In particular, the one-pot hydrodeoxygenation of the C9 carbonyl compounds (e.g. aldehydes and/or ketones) may occur in the presence of the first and second catalysts and a constant pressure of H$_2$ gas. The hydrodeoxygenation reaction may be carried out under any conditions suitable to progress the reaction toward the production of the relevant corresponding alkenes and/or alkanes. For example, the reaction may be carried out under any suitable heat and constant pressure conditions. In some embodiments, for example, a reaction vessel including a reaction mixture of the C9 carbonyl compounds (e.g. aldehydes and/or ketones), and the first and second catalysts may be purged with H$_2$ and then pressurized to a suitable pressure (e.g., 100 to 350 psig, or 200 to 300 psig) which is then held constant until H$_2$ consumption by the reaction ceases. The reaction vessel may also be heated to a suitable temperature to drive the reaction. According to embodiments of the present invention, the reaction temperature may be relatively low, e.g., about 80° C. to about 200° C., or about 100° C. to about 150° C. The vessel may be subjected to these conditions for any suitable amount of time to complete the reaction, as determined by the cessation of H$_2$ consumption. For example, in some embodiments, the reaction time may be about 10 hours to about 30 hours, or about 14 hours to about 24 hours.

In some embodiments, the one-pot hydrodeoxygenation of the C9 carbonyl compounds (either separately or together) may occur in the presence of the first and second catalysts and a solvent (e.g., cyclohexane and/or hexadecane). The hydrodeoxygenation reaction may be carried out under any conditions suitable to progress the reaction toward the production of the relevant corresponding alkenes and/or alkanes. For example, the reaction may be carried out under any suitable heat and constant pressure conditions. In some embodiments, for example, a reaction vessel including a reaction mixture of the C9 carbonyl compounds (e.g. aldehydes and/or ketones), the first and second catalysts, and the solvent may be purged with H$_2$ and then pressurized to a suitable pressure (e.g., 150 to 350 psig, or 200 to 300 psig). The reaction vessel may also be heated to a suitable temperature to drive the reaction. According to embodiments of the present invention, the reaction temperature may be relatively low, e.g., about 80° C. to about 200° C., or about 100° C. to about 150° C. The vessel may be subjected to these conditions for any suitable amount of time to complete the reaction. For example, in some embodiments, the reaction time may be about 2 hours to about 10 hours, or about 3 hours to about 5 hours.

The one-pot hydrodeoxygenation processes according to embodiments of the present invention may also be used to convert technical grade and/or commercially available C$_9$H$_{18}$O (e.g., technical grade C$_9$H$_{18}$O available as #537691 from Sigma-Aldrich Co. LLC) to C9 alkanes (e.g., 2,6-dimethylheptane and 2,4-dimethylheptane).

ONE-POT HYDRODEOXYGENATION EXAMPLES

The following one-pot hydrodeoxygenation examples are provided for illustrative purposes only, and do not limit the scope of the embodiments of the present invention.

One-Pot Hydrodeoxygenation Example 1—Hydrodeoxygenation of DIBK

Figure 3A:
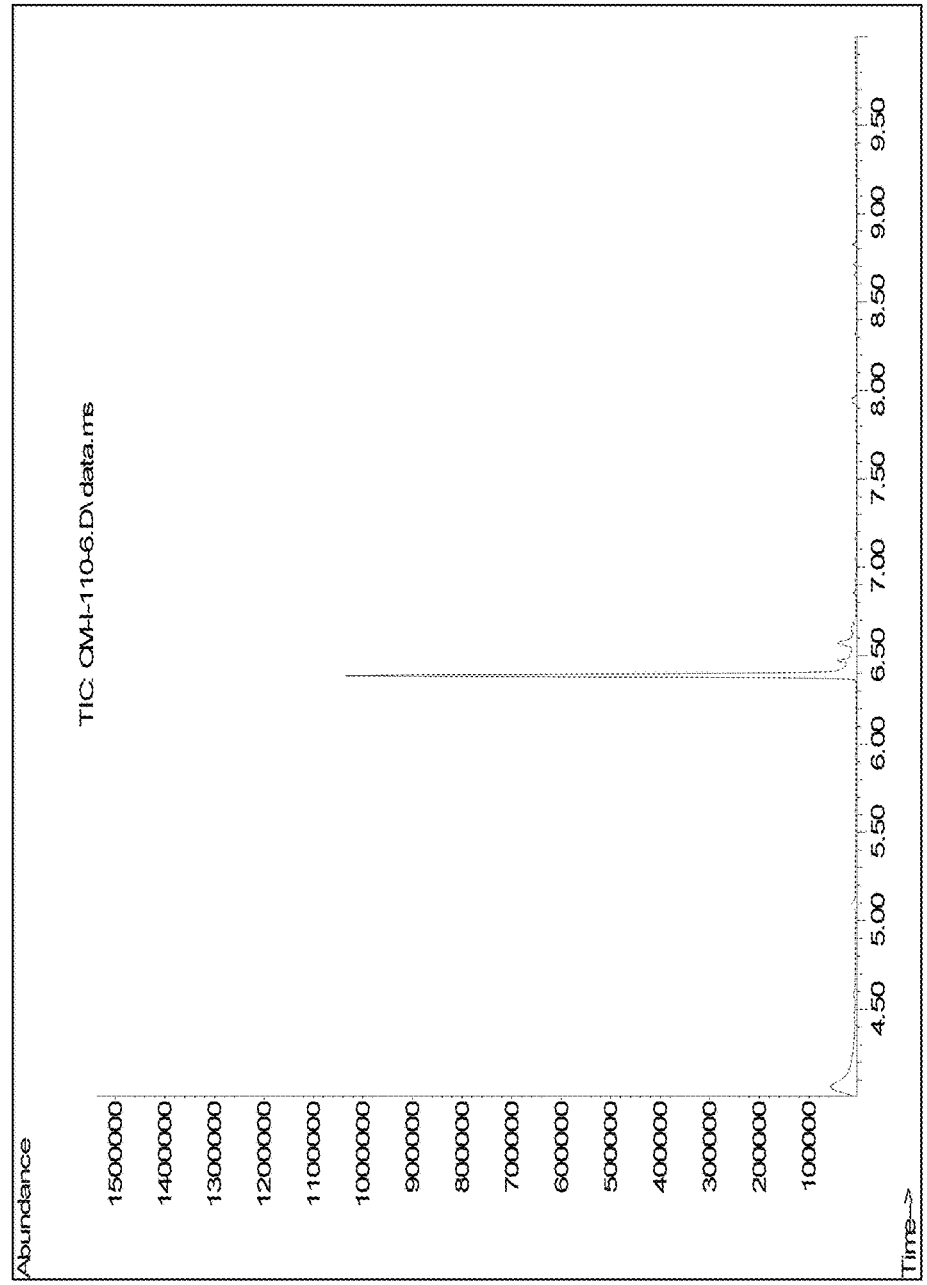
FIGS. 3A and 3B depict the GC-MS spectrum of the reaction product achieved from the process of One-pot Hydrodeoxygenation Example 1.
Figure 3B:
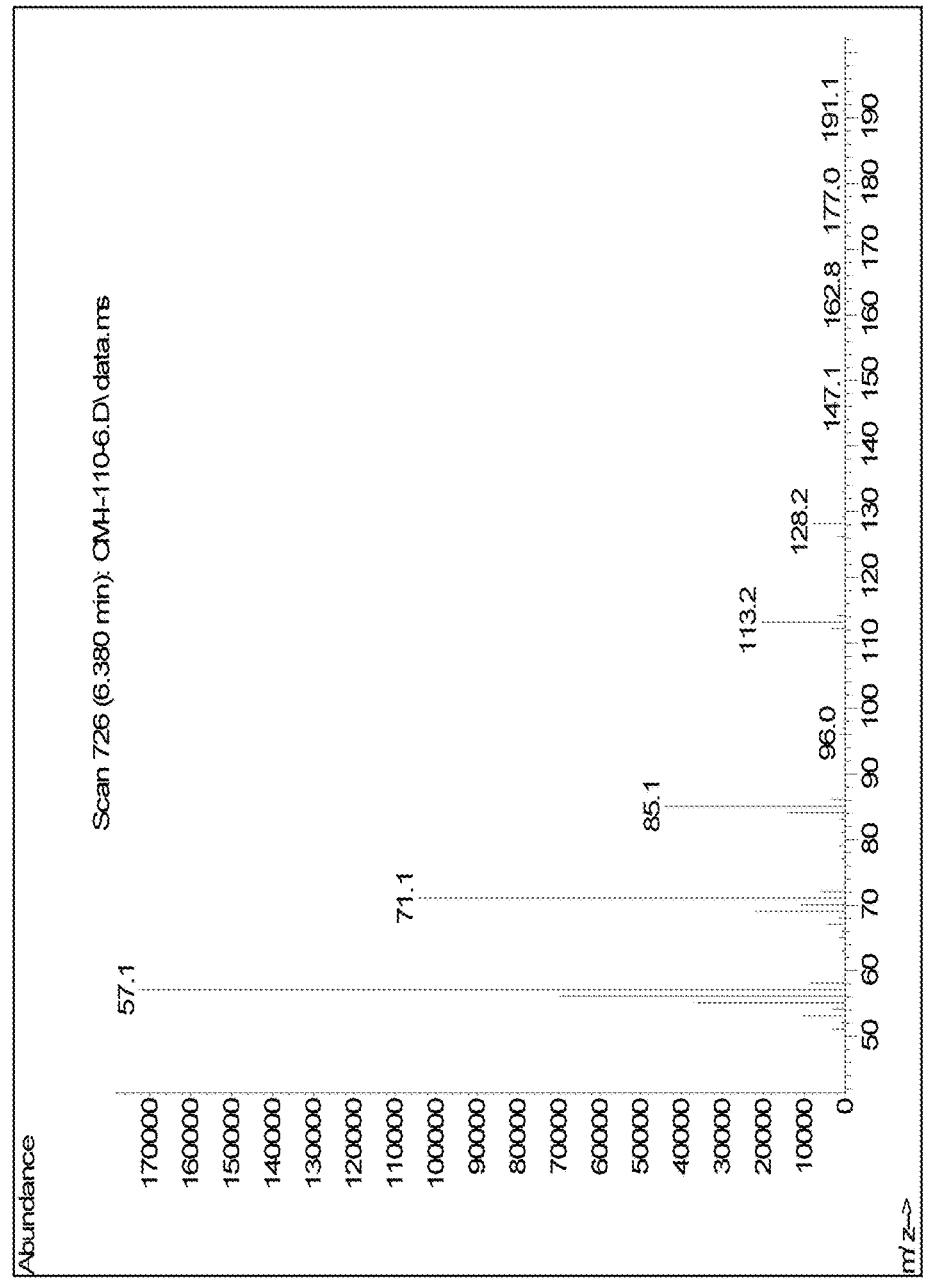
Figure 4A:
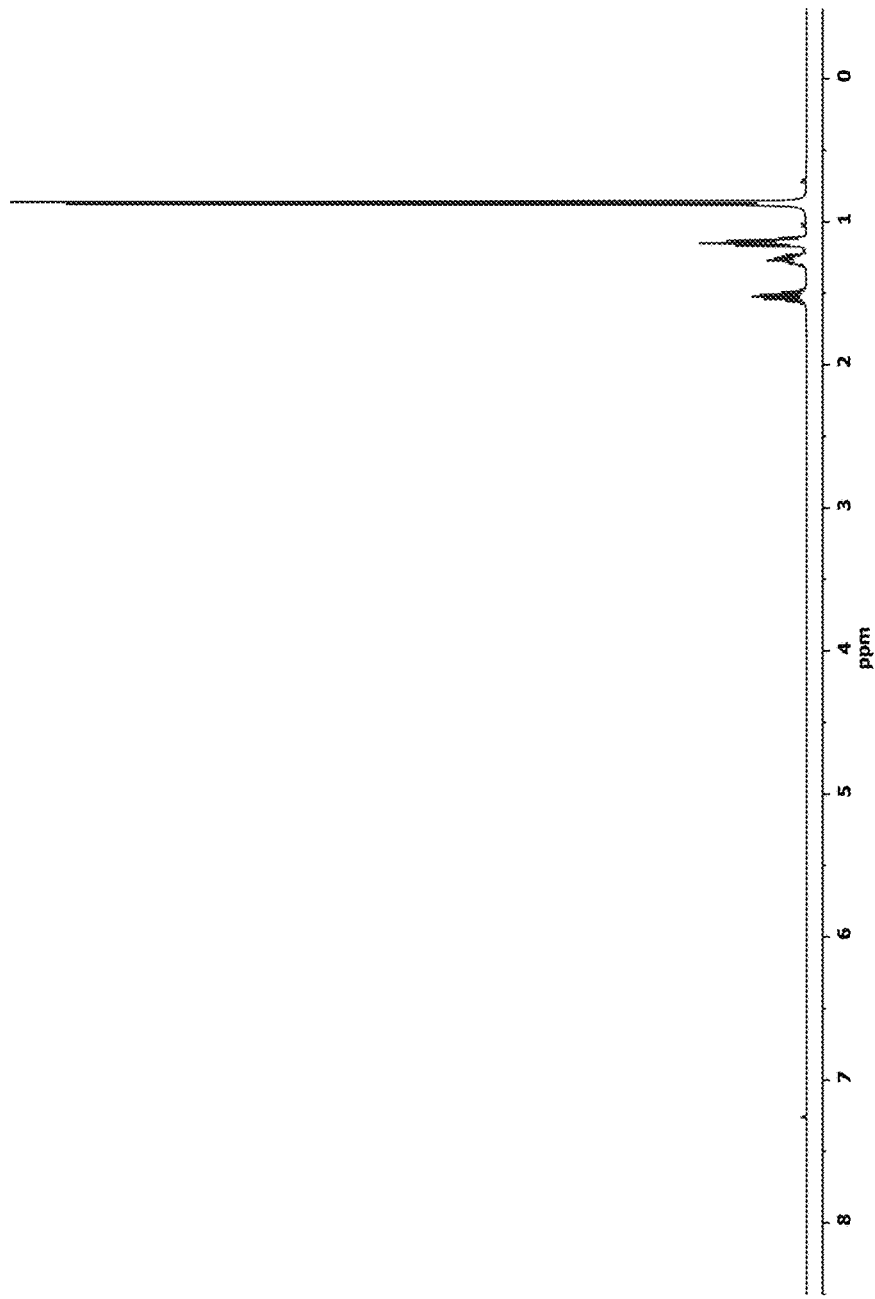
FIGS. 4A and 4B depict the 1H NMR (400 MHz) spectrum of the reaction product achieved from the process of One-pot Hydrodeoxygenation Example 1.
Figure 4B:
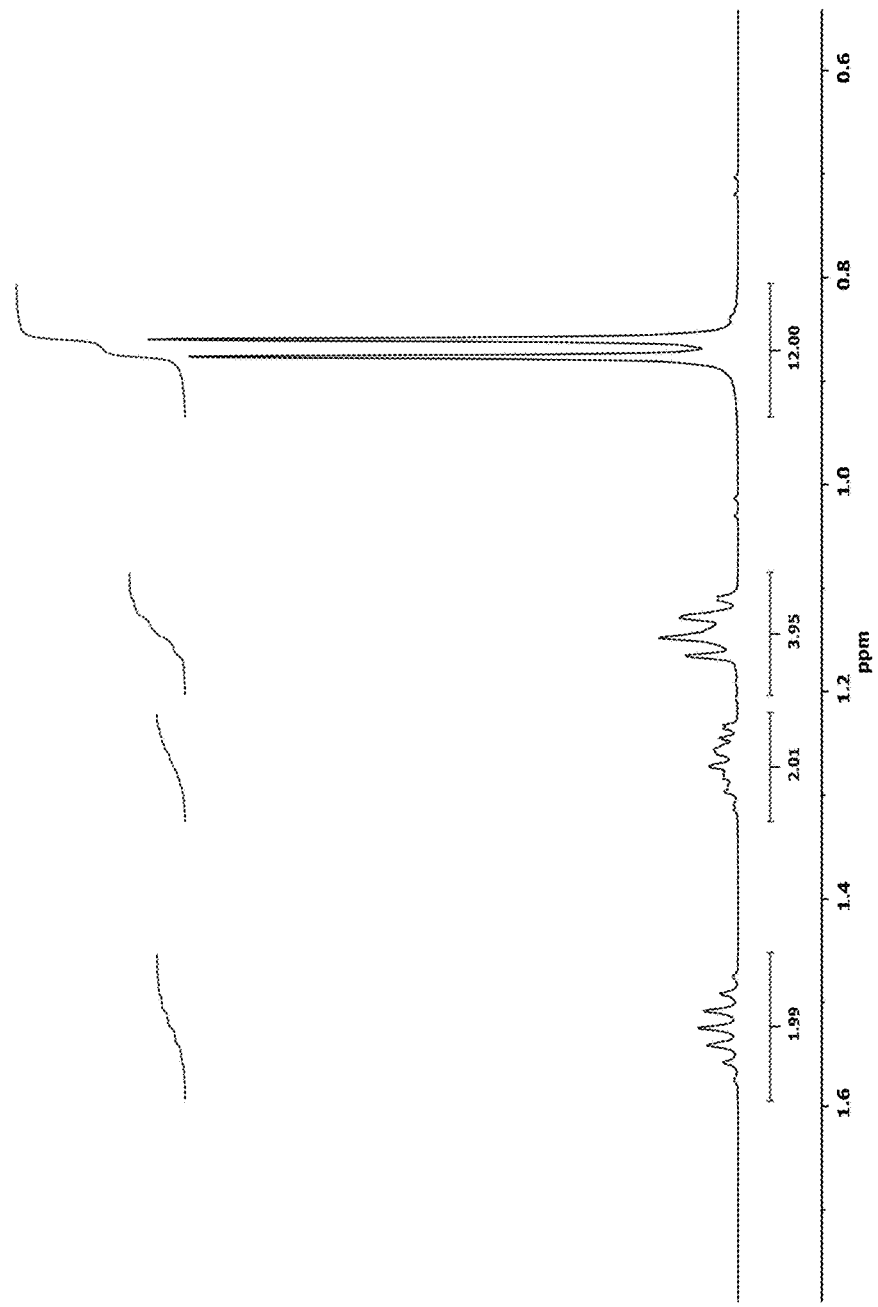
Figure 5A:
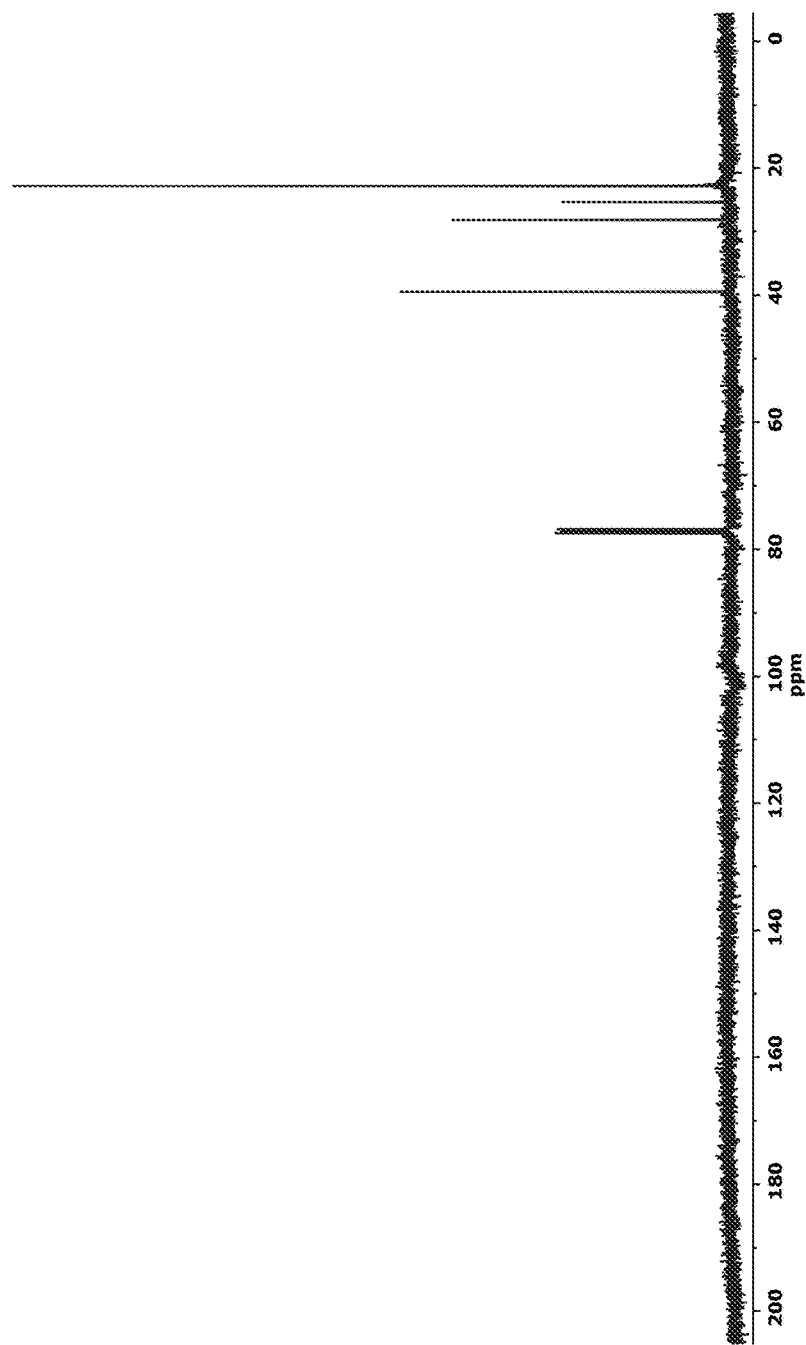
FIGS. 5A and 5B depict the 13C NMR (101 MHz) spectrum of the reaction product achieved from the process of One-pot Hydrodeoxygenation Example 1.
Figure 5B:
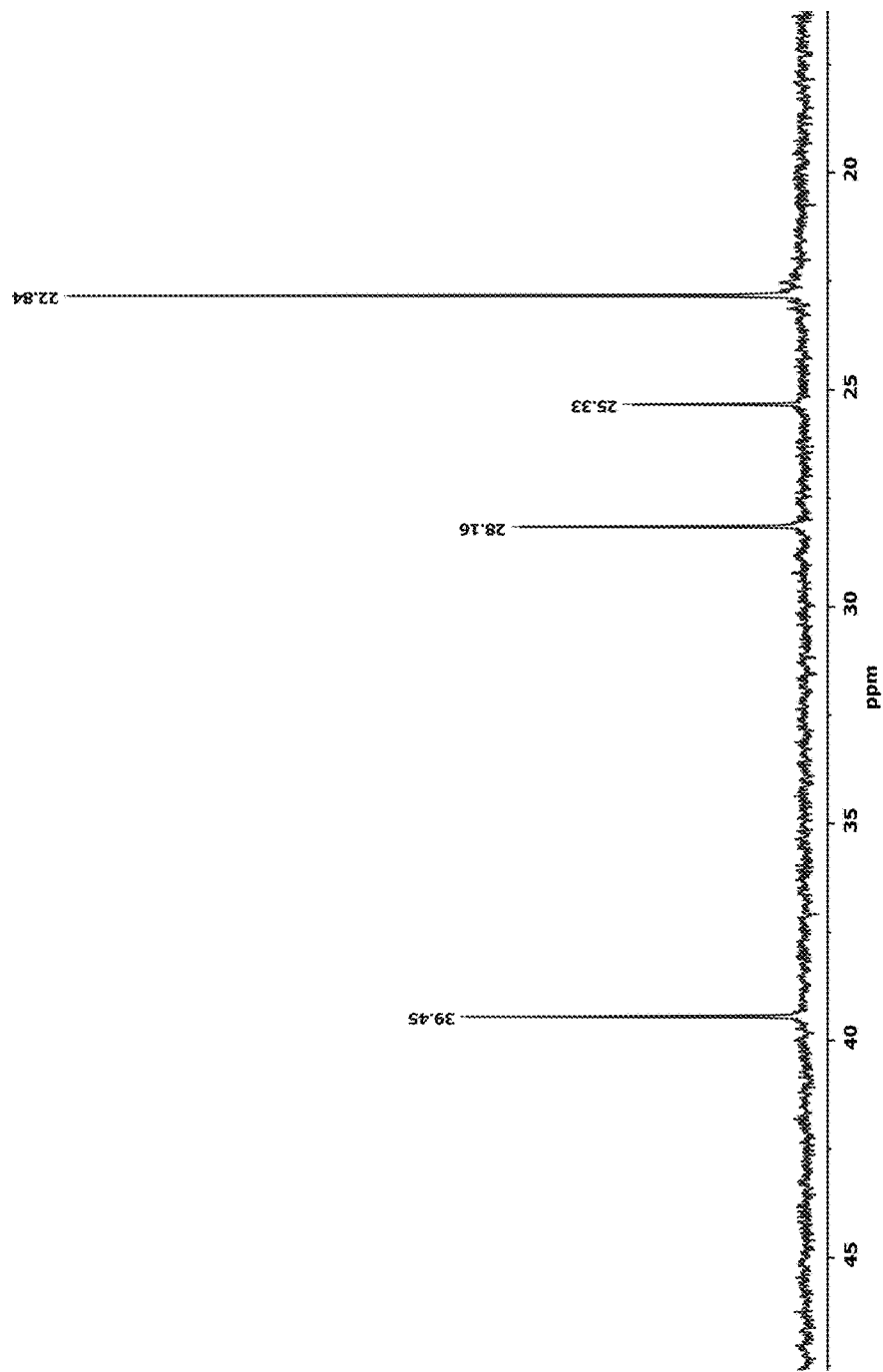

Diisobutyl ketone (4.0 mL; 22.7 mmol), Ni/SiO$_2$—Al$_2$O$_3$ (0.30 g; 65 wt % Ni, 3.32 mmol) and Amberlyst 15 (0.15 g)

were loaded into a 50 mL stainless steel bomb reactor fitted with an overhead stirring device. The reactor was connected to a high pressure gas burette (150 mL, 480 psig $H_2$; ca. 200 mmol $H_2$) to maintain a constant $H_2$ pressure inside the reactor and monitor $H_2$ consumption. The reactor was purged with $H_2$ and then pressurized to 300 psig and heated to 120° C. After $H_2$ consumption ceased (about 22 hours), the reactor was cooled and slowly vented. GC-MS analysis (shown in FIGS. 3A and 3B) of an aliquot of the reaction mixture revealed quantitative formation of the desired product. The solution was filtered to remove the catalysts and provide pure 2,6-dimethylheptane as a colorless liquid (2.17 g; 74%). The $^1$H NMR (400 MHz) spectrum of the 2,6-dimethylheptane is depicted in FIGS. 4A and 4B, and the $^{13}$C NMR (101 MHz) spectrum is depicted in FIGS. 5A and 5B. $^1$H NMR (400 MHz, $CDCl_3$) δ 1.51 (nonet, J=6.6 Hz, 2H), 1.32-1.20 (m, 2H), 1.19-1.08 (m, 4H), 0.87 (d, J=6.6 Hz, 12H). $^{13}$C NMR (101 MHz, $CDCl_3$) δ 39.45, 28.16, 25.33, 22.84.

One-Pot Hydrodeoxygenation Example 2—DIBK

Diisobutyl ketone (2.0 mL; 11.4 mmol), Ni/$SiO_2$—$Al_2O_3$ (0.15 g; 65 wt % Ni, 1.66 mmol), Amberlyst 15 (0.15 g) and cyclohexane (8 mL) were loaded into a 50 mL stainless steel bomb reactor fitted with an overhead stirring device. The reactor was purged with $H_2$ and then pressurized to 300 psig and heated to 120° C. After 4.5 hours, the reactor was cooled and slowly vented. GC-MS analysis of an aliquot of the reaction mixture revealed quantitative formation of the desired product. The solution was filtered to remove the catalysts and 2,6-dimethylheptane was obtained as a colorless liquid (1.14 g; 78%) after removing cyclohexane via distillation.

One-Pot Hydrodeoxygenation Example 3—DIBK

One-pot hydrodeoxygenation of DIBK was carried out as in One-pot Hydrodeoxygenation Example 2, except that hexadecane was used instead of cyclohexane. GC-MS analysis of an aliquot of the reaction mixture revealed quantitative formation of the desired product. No attempt was made to isolate 2,6-dimethylheptane from the solvent.

One-Pot Hydrodeoxygenation Example 4—Technical Grade $C_9H_{18}O$

Figure 6A:
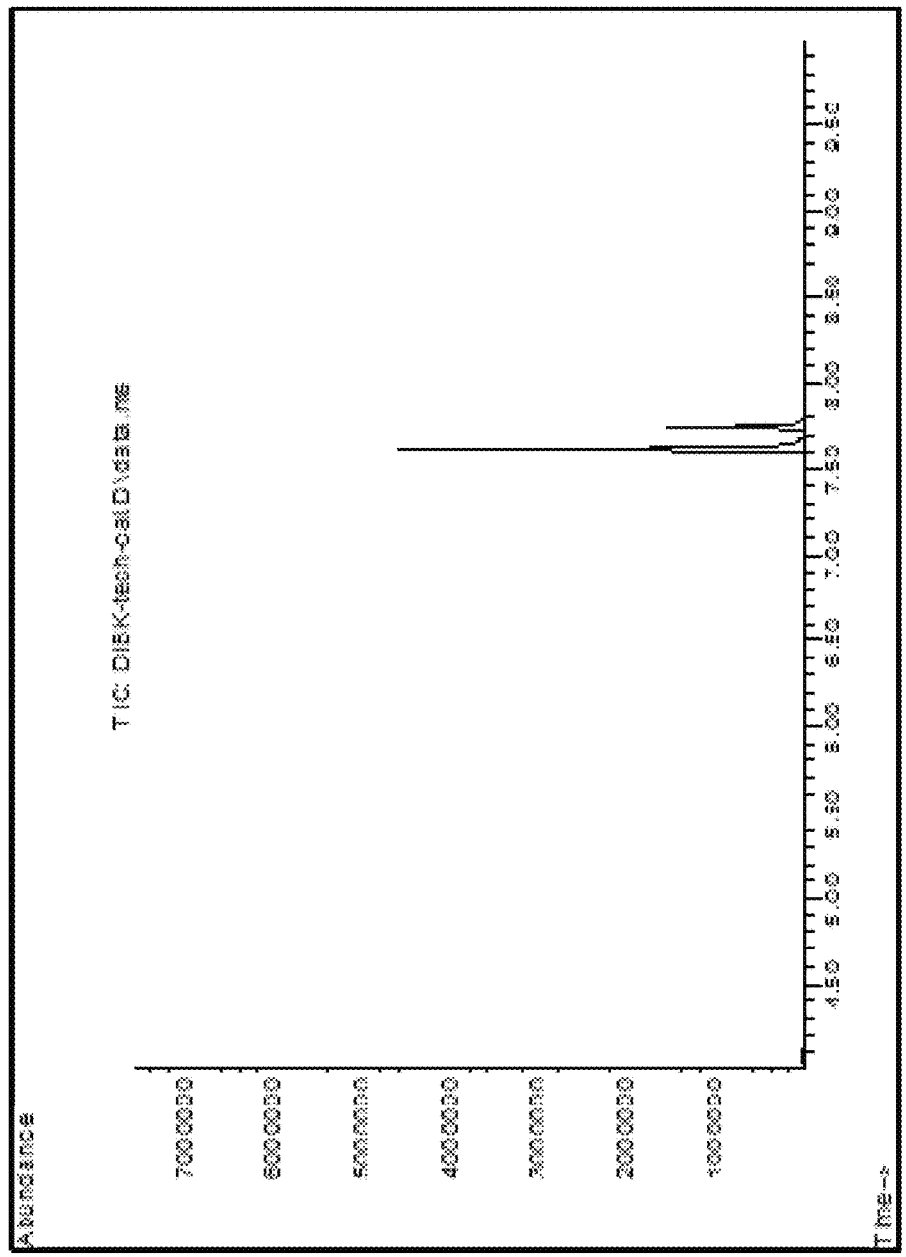
FIGS. 6A through 6C depict the GC-MS analysis of as-received technical grade $C_9H_{18}O$ (Sigma Aldrich#537691, lot#MKBT3519V) as the starting material in One-pot Hydrodeoxygenation Example 4, showing 2,6-Dimethyl-4-heptanone (7.62 min) and 4,6-dimethyl-2-heptanone (7.74 min) present in an 8:3 ratio, respectively.
Figure 6B:
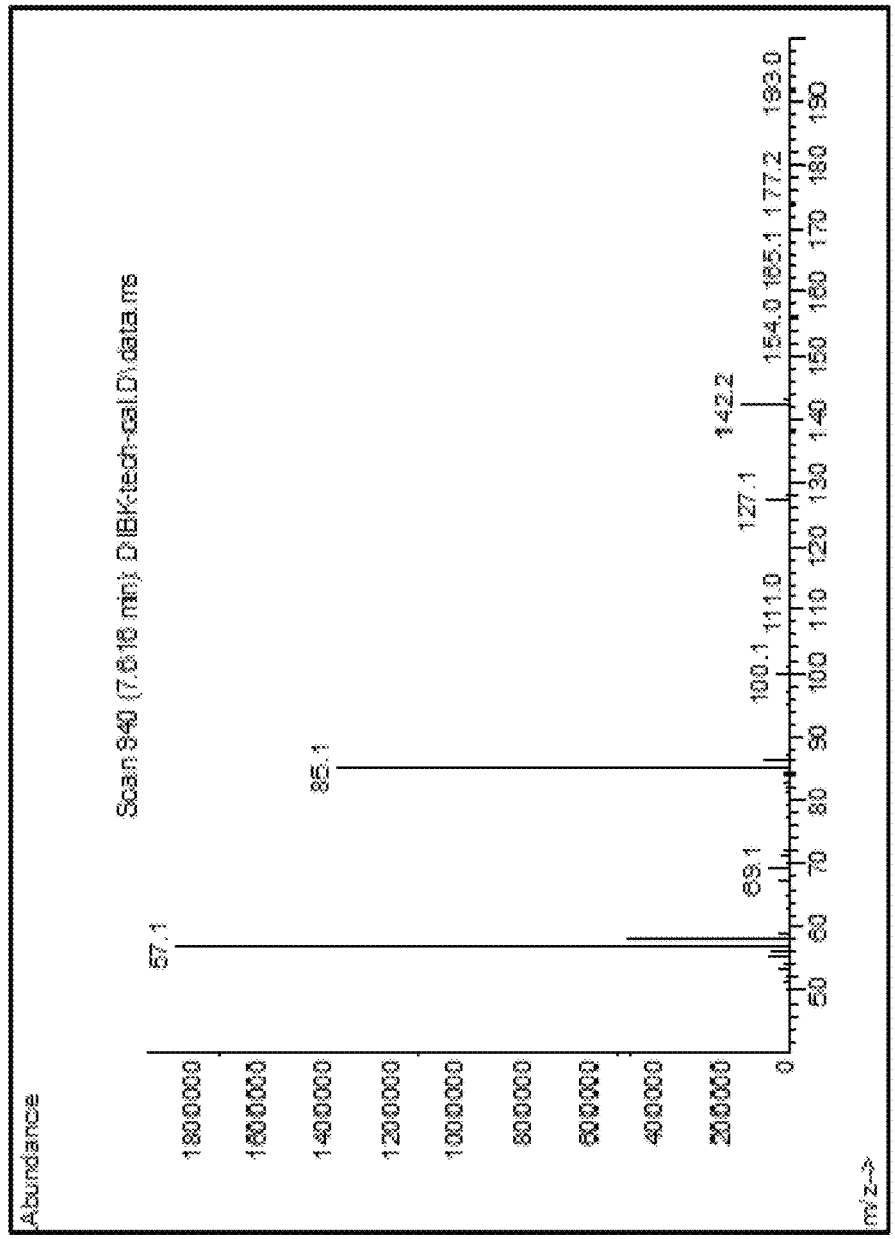
Figure 6C:
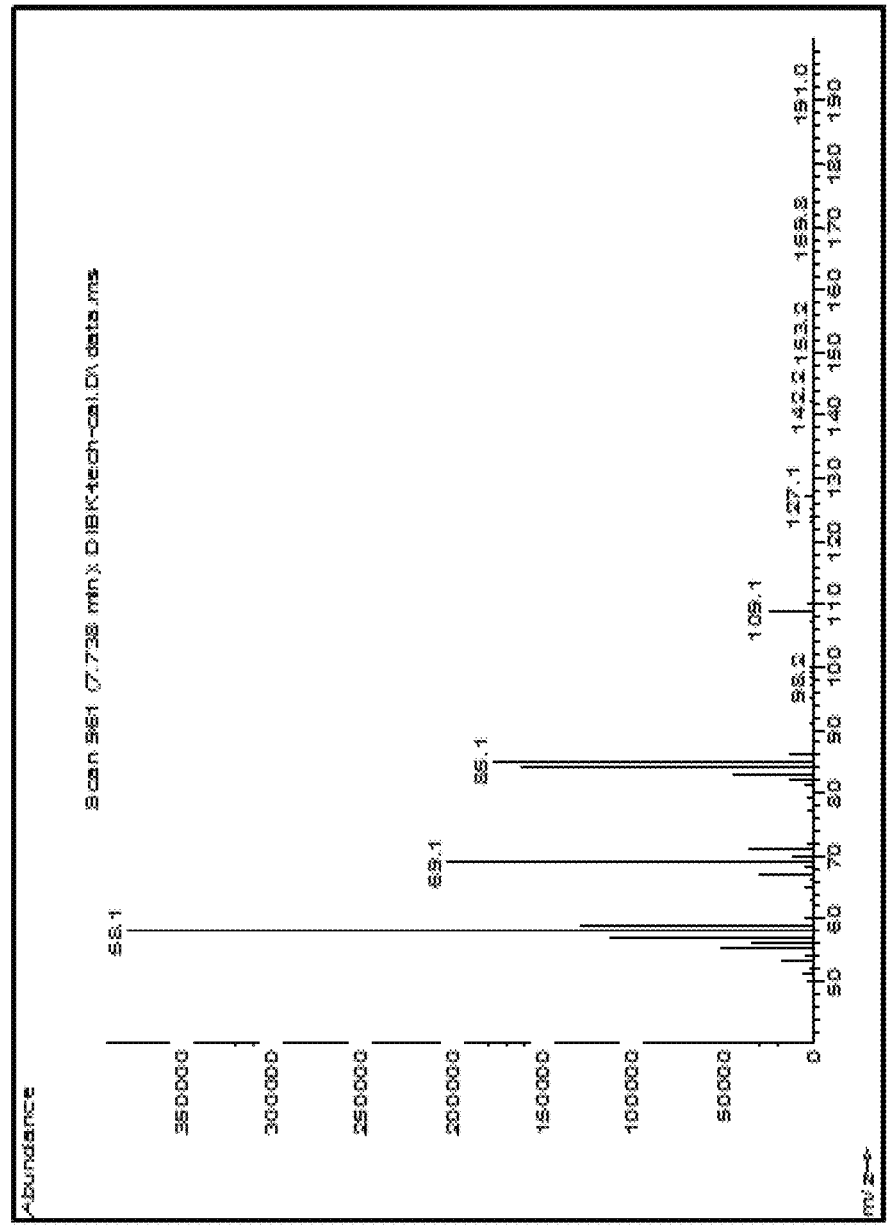
Figure 6D:
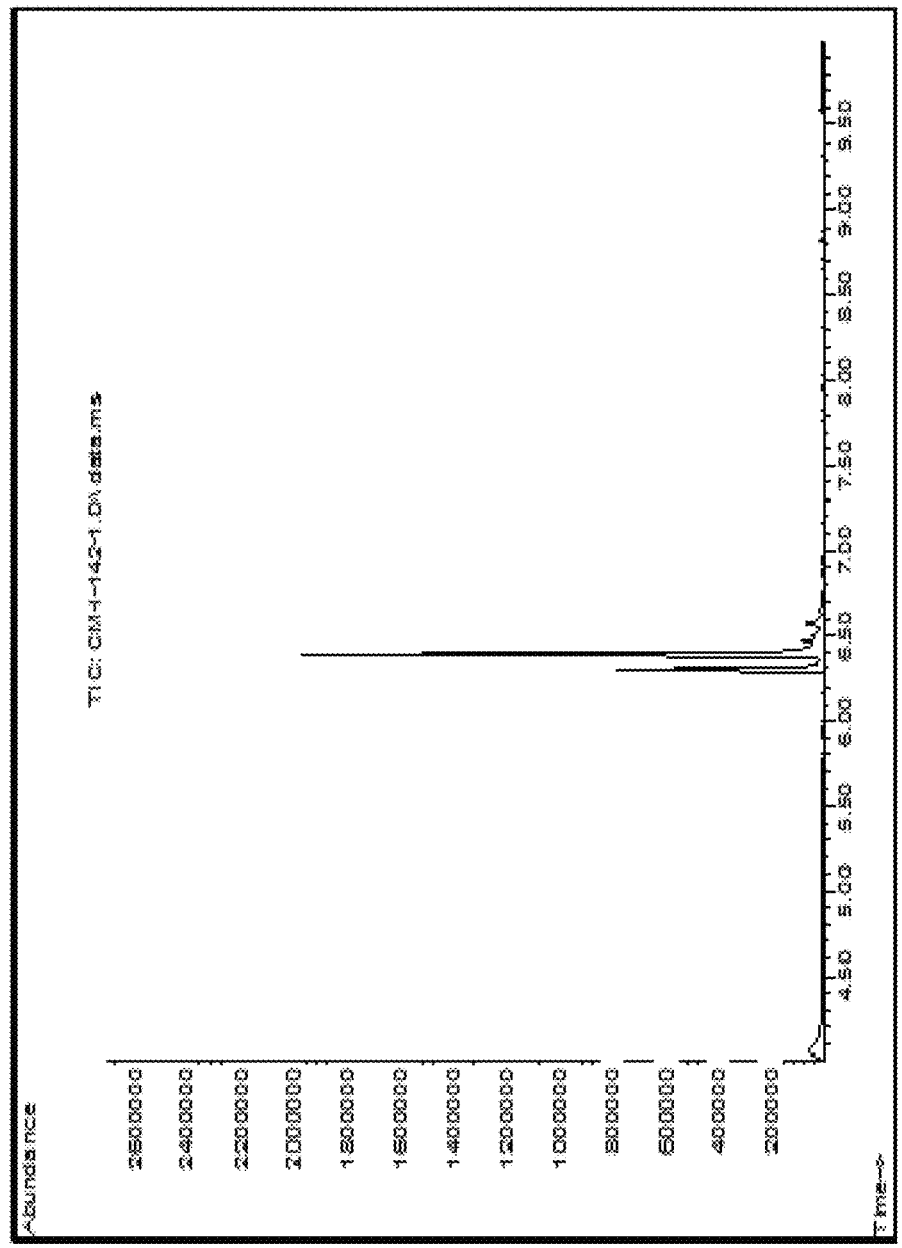
FIGS. 6D through 6F depict the GC-MS analysis of the $C_9H_{20}$ isomers obtained via hydrodeoxygenation according to One-pot Hydrodeoxygenation Example 4 of technical grade $C_9H_{18}O$, showing 2,6-Dimethylheptane (6.39 min) and 2,4-dimethylheptane (6.30 min) present in an 8:3 ratio, respectively.
Figure 6E:
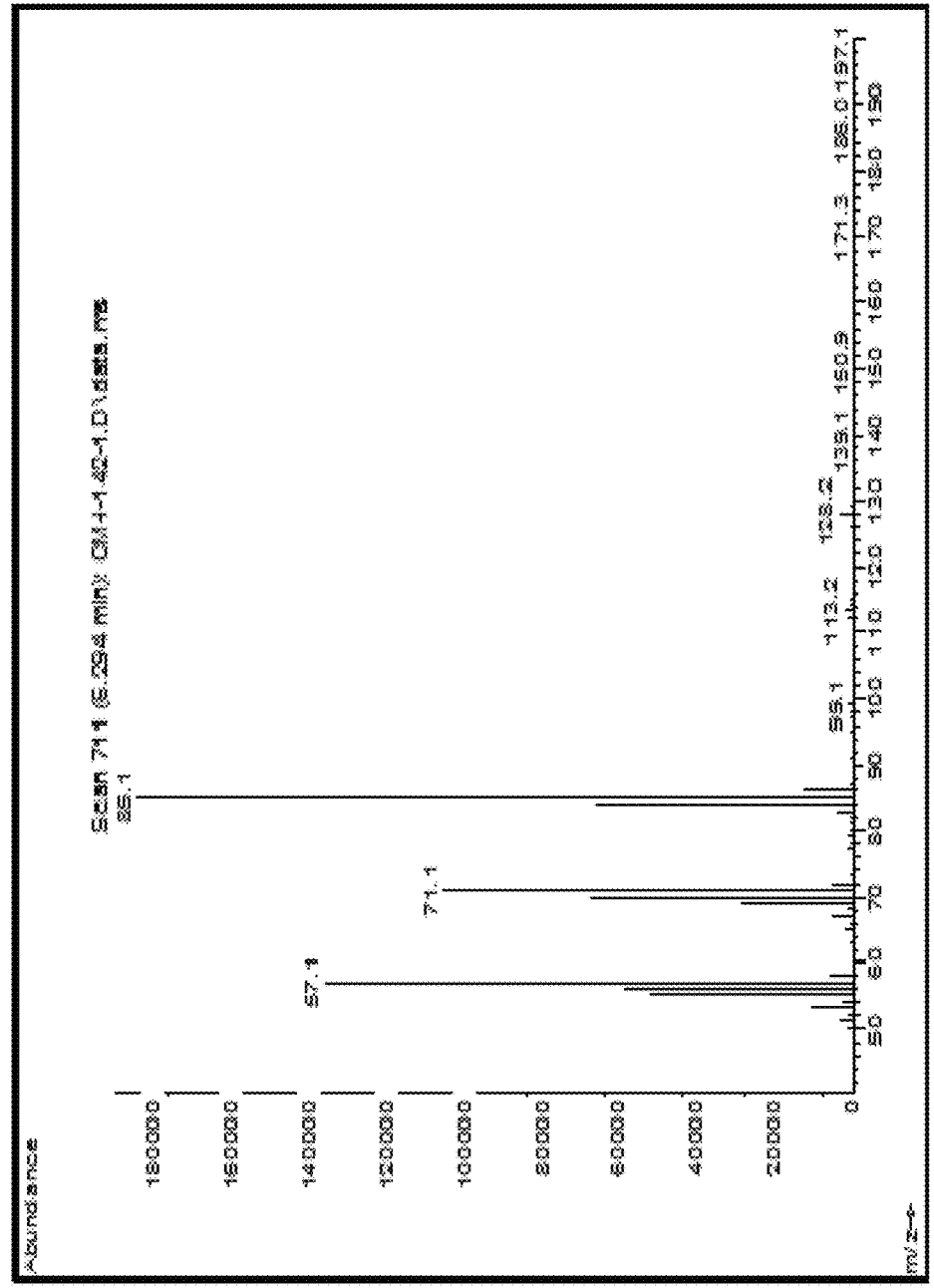
Figure 6F:
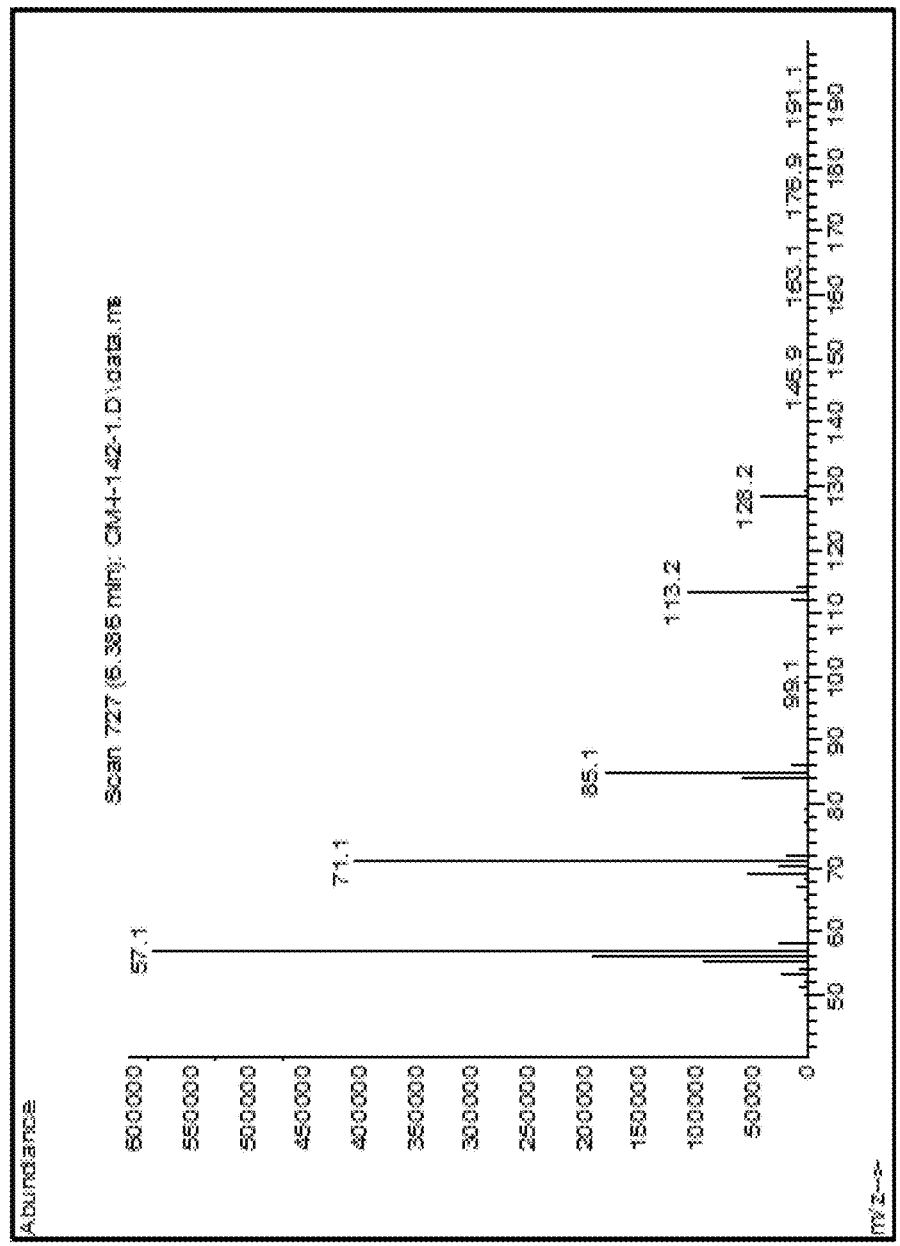
Figure 7A:
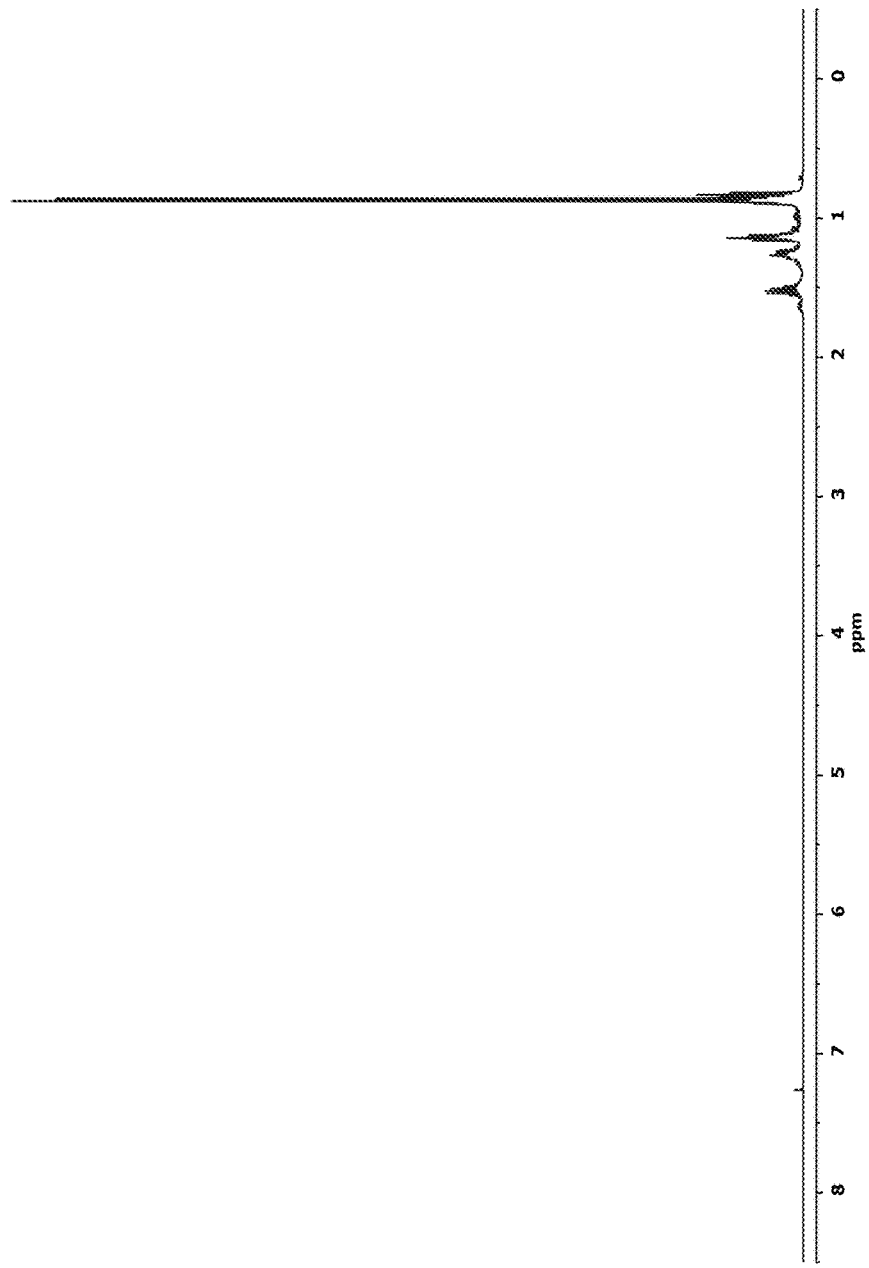
FIGS. 7A and 7B depict the 1H NMR (400 MHz) spectrum of the $C_9H_{20}$ isomers obtained via hydrodeoxygenation of technical grade $C_9H_{18}O$ according to One-pot Hydrodeoxygenation Example 4.
Figure 7B:
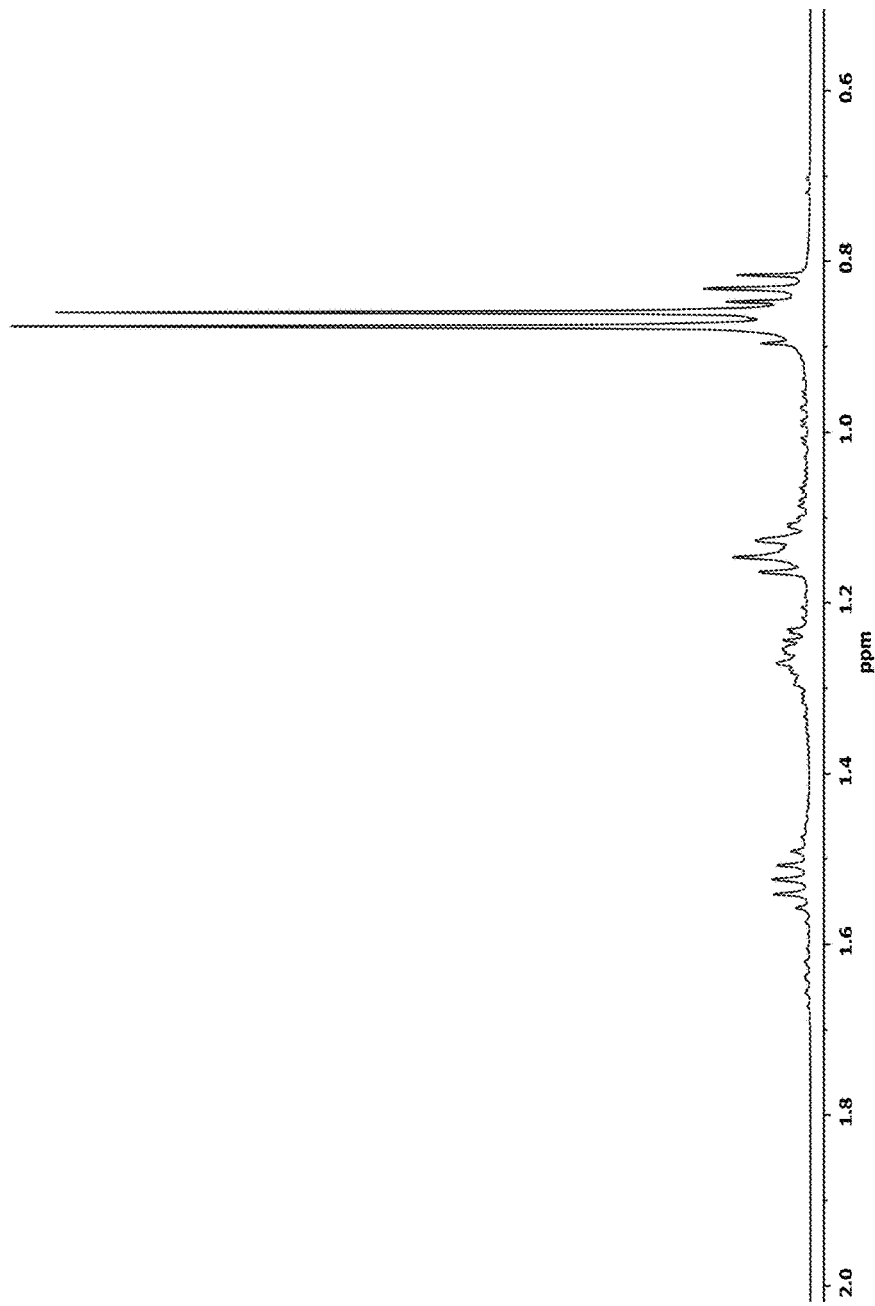
Figure 8A:
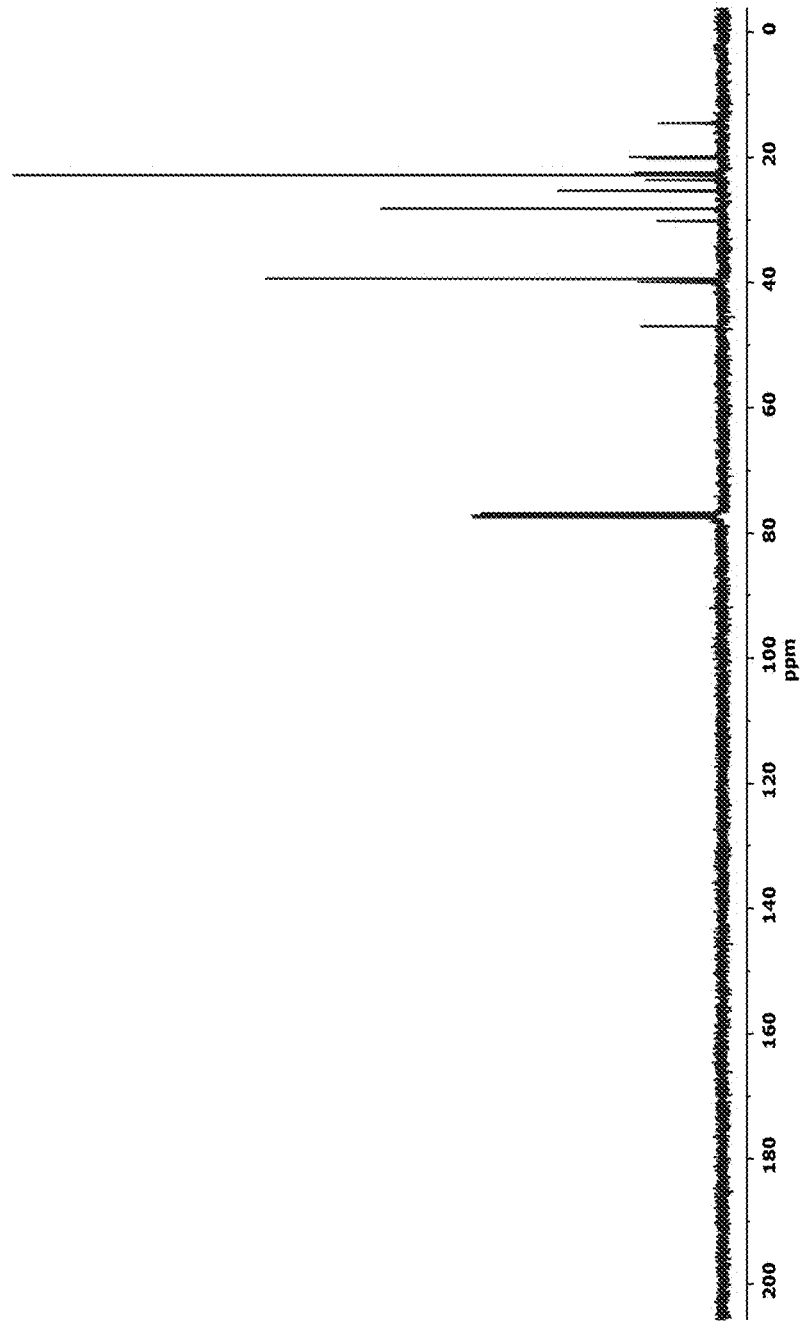
FIGS. 8A and 8B depict the 13C NMR (101 MHz) spectrum of $C_9H_{20}$ isomers obtained via hydrodeoxygenation of technical grade $C_9H_{18}O$ to 2,4-dimethylheptane (denoted *) and 2,6-dimethylheptane (denoted #) according to One-pot Hydrodeoxygenation Example 4.
Figure 8B:
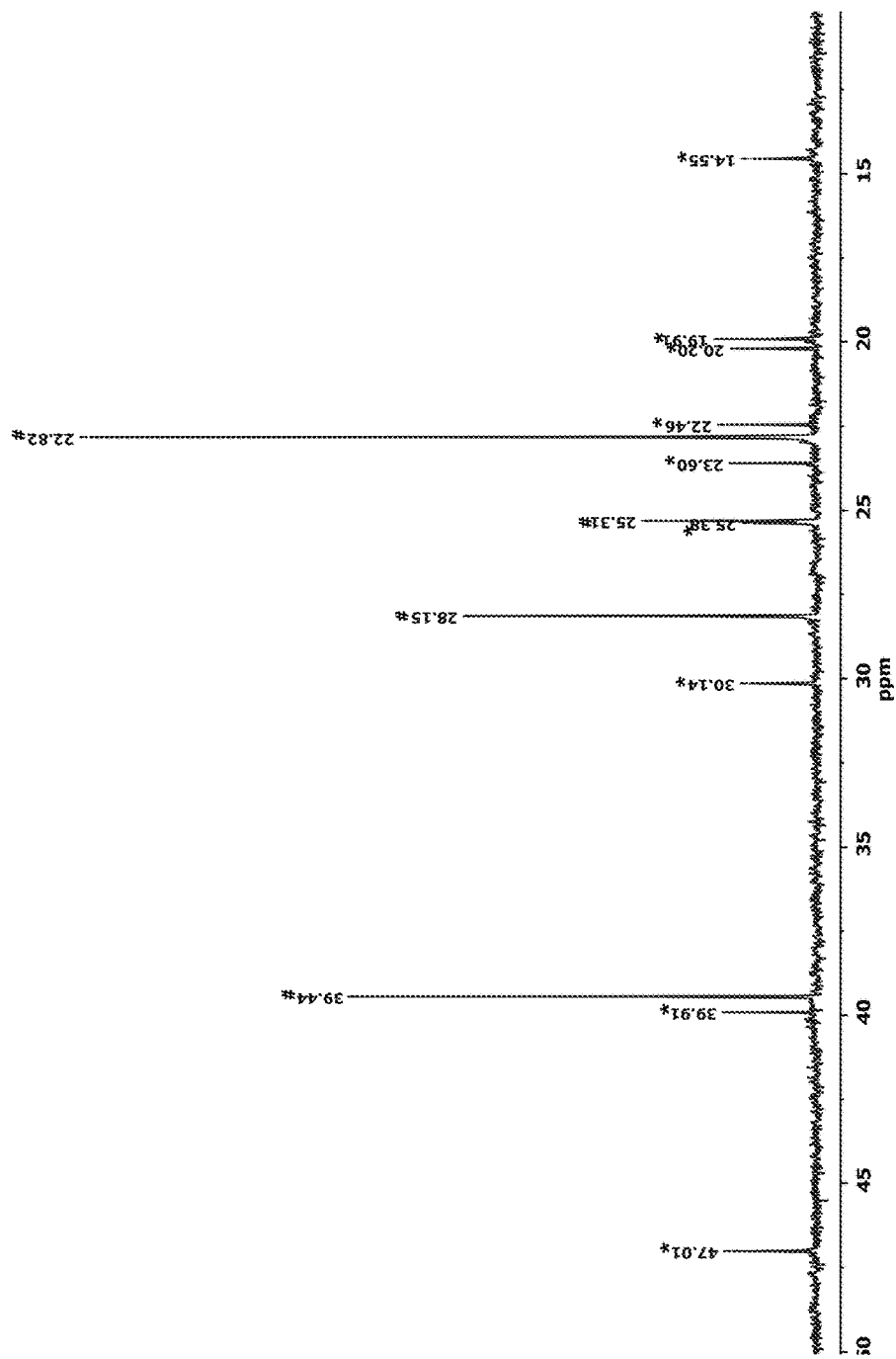

As-received technical grade $C_9H_{18}O$ (2.92 g; 22.8 mmol: Sigma Aldrich#537691, lot# MKBT3519V), Ni/$SiO_2$—$Al_2O_3$ (0.30 g; 65 wt % Ni, 3.32 mmol) and Amberlyst 15 (0.16 g) were loaded into a 50 mL stainless steel bomb reactor fitted with an overhead stirring device. The reactor was connected to a high pressure gas burette (150 mL, 500 psig $H_2$; about 210 mmol $H_2$) to maintain a constant $H_2$ pressure inside the reactor and monitor $H_2$ consumption. The reactor was purged with $H_2$ and then pressurized to 300 psig and heated to 120° C. After $H_2$ consumption ceased (about 17 h), the reactor was cooled and slowly vented. GC-MS analysis of an aliquot of the reaction mixture revealed quantitative conversion to a mixture of 2,6-dimethylheptane and 2,4-dimethylheptane. The solution was filtered to remove the catalysts and provide a colorless liquid of the two $C_9H_{20}$ isomers (2.25 g; 77%). The GC-MS analysis is shown in FIGS. 6A through 6C, the $^1$H NMR (400 MHz) spectrum is depicted in FIGS. 7A and 7B, and the $^{13}$C NMR (101 MHz) spectrum is depicted in FIGS. 8A and 8B. $^{13}$C NMR (101 MHz, $CDCl_3$) δ 39.91, 28.15, 25.31, 22.82 (2,6-dimethylheptane); 47.01, 39.44, 30.14, 25.38, 23.60, 22.46, 20.20, 19.91, 14.55 (2,4-dimethylheptane).

Figure 9:
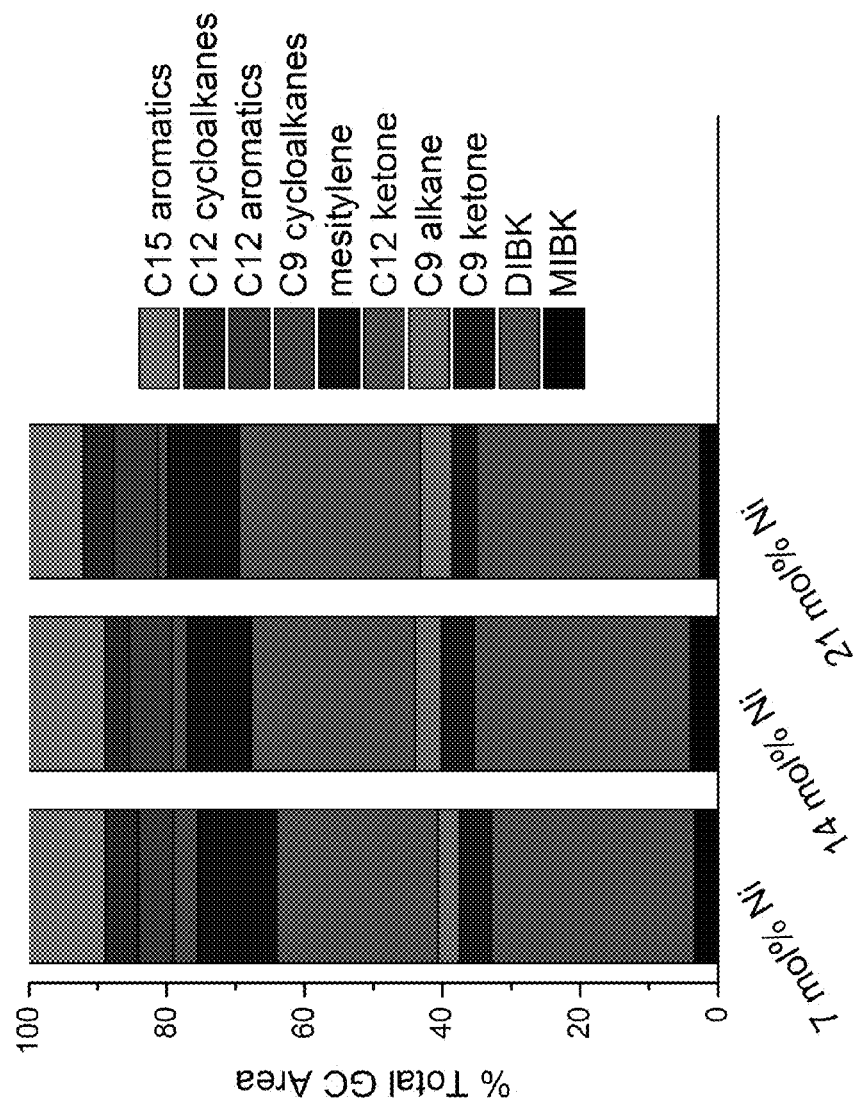
FIG. 9 is a graph depicting the effect of second catalyst (e.g., Ni) loading on product distribution in an acetone condensation scheme using $Ni/SiO_2$—$Al_2O_3$ and Amberlyst 15 at 120° C., with the different products shown in the indicated colors as shown in the drawing legend.
Figure 10:
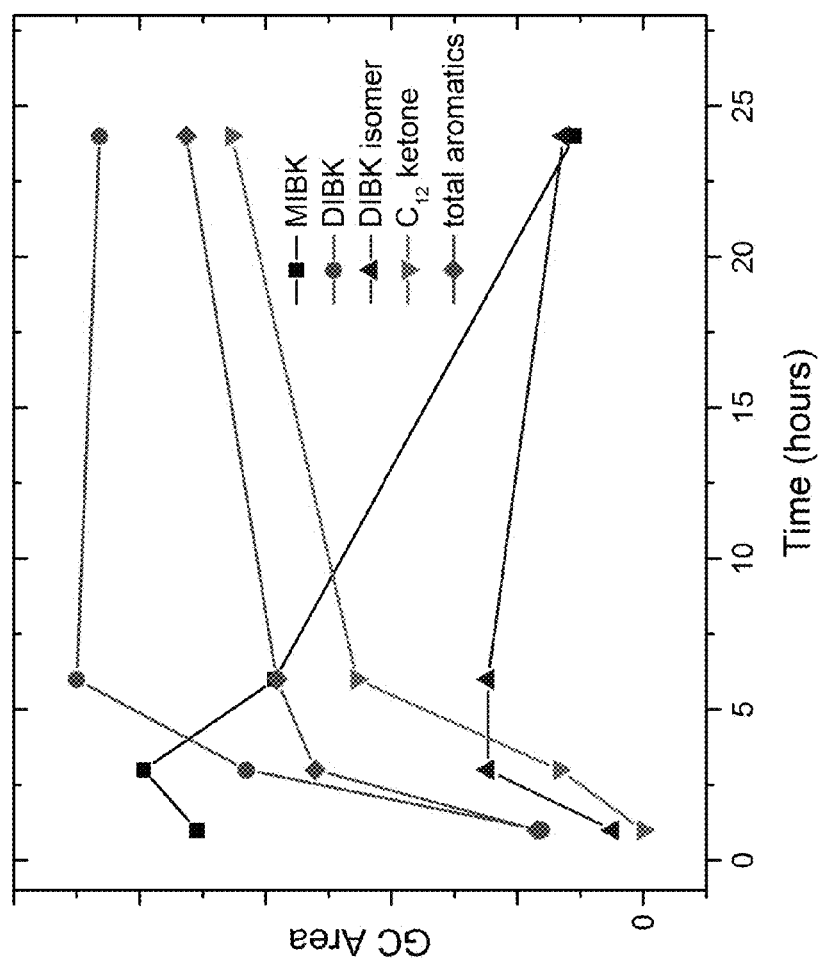
FIG. 10 is a graph depicting the time profile for acetone condensation products using $Ni/SiO_2$—$Al_2O_3$ and Amberlyst 15 at 120° C., with MIBK shown in black, DIBK shown in red, DIBK isomer shown in blue, $C_{12}$ ketone shown in pink, and total aromatics shown in green.
Figure 11:
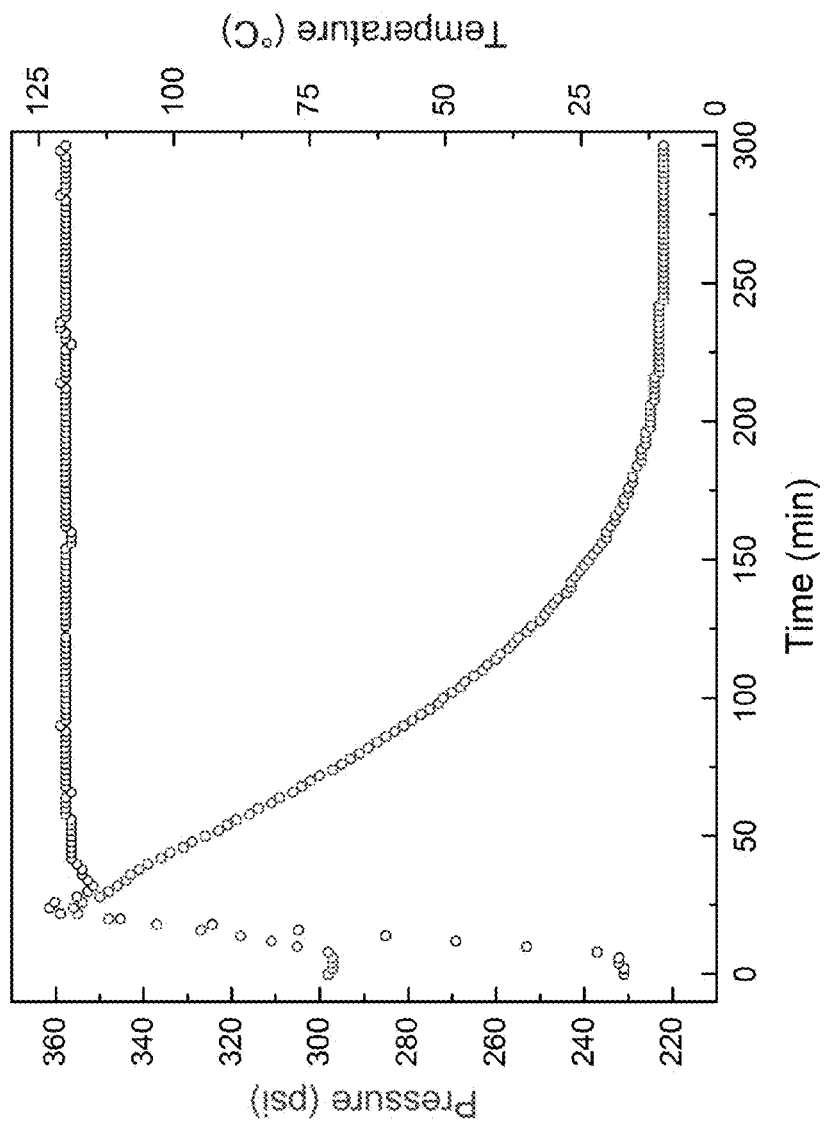
FIG. 11 is a kinetic trace of $H_2$ consumption during the hydrodeoxygenation of 2,6-dimethyl-4-heptanone using $Ni/SiO_2$—$Al_2O_3$ and Amberlyst 15 at 120° C., with the blue trace showing consumption according to temperature and the red trace showing consumption according to pressure.
Figure 12A:
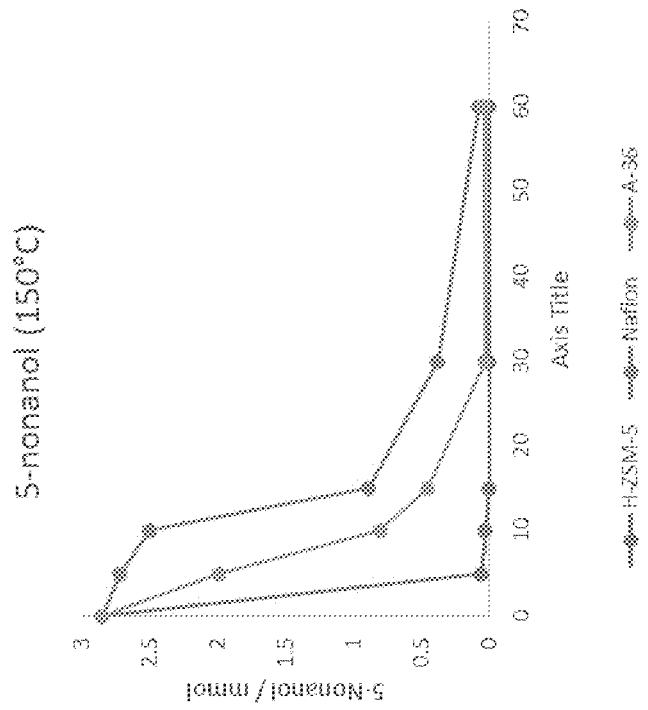
FIGS. 12A through 12C depict the conversion of nonanol to nonene using various different catalysts at three different temperatures (i.e., 120° C.
Figure 12B:
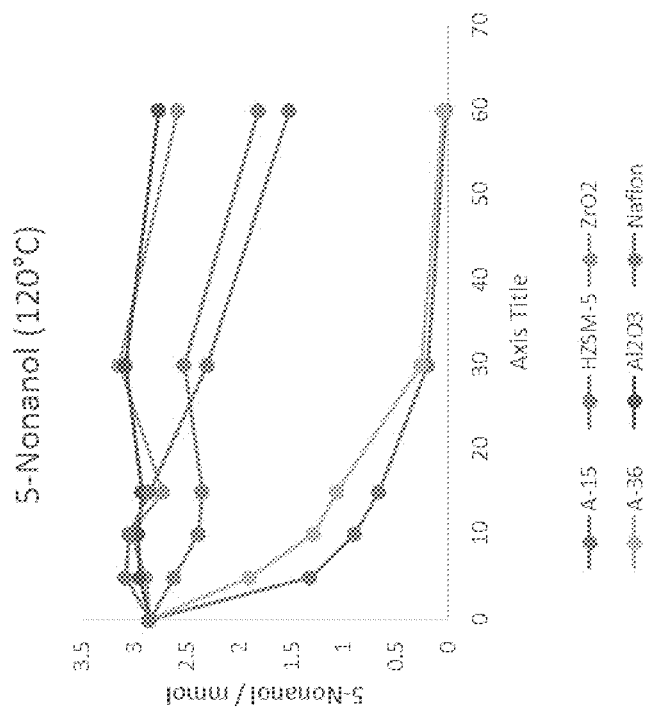
Figure 12C:
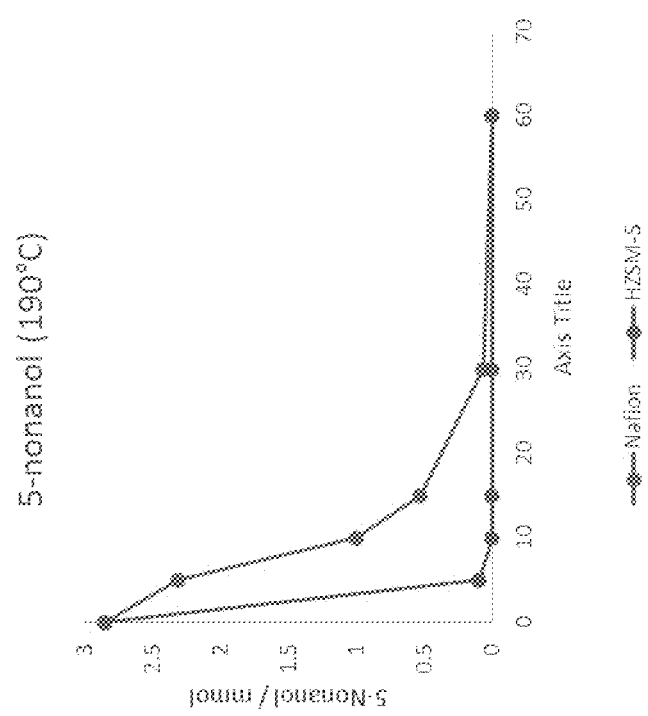

As discussed above, the reactions and processes according to embodiments of the present invention can be tuned to yield differing amounts of the various carbonyl compounds (e.g. aldehydes and/or ketones), alcohol products, alkenes and/or alkanes produced. To tune the yields of the different carbonyl compounds (e.g. aldehydes and/or ketones), alcohol products, alkenes and/or alkanes, the reaction parameters may be adjusted in different ways depending on the desired outcome. For example, the second catalyst loading can adjust the resulting yield of DIBK, MIBK, the C9 ketone, the C9 alkane and the C12 ketone, as shown in the graph depicted in FIG. 9 (showing C15 aromatics in olive, C12 cycloalkanes in burgundy, C12 aromatics in purple, C9 cycloalkanes in lavender, mesitylene in navy blue, C12 ketones in green, C9 alkanes in pink, C9 ketones in royal blue, DIBK in red, and MIBK in black). Additionally, FIGS. 10 (time profile of the reaction) and 11 (kinetic trace of H2 consumption during hydrodeoxygenation of 2,6-dimethyl-4-heptanone) show the role time, pressure and temperature play in the tunability of the processes according to embodiments of the present invention (in which FIG. 10 shows MIBK in black, DIBK in red, DIBK isomer in blue, C12 ketone in pink, and total aromatics in green, and FIG. 11, shows pressure in red and temperature in blue). Also, the selections of different catalysts for the first and second catalysts provide tunability, as shown in FIGS. 12A (showing A-15 in aquamarine, HZSM-5 in orange, $ZrO_2$ in gray, A-36 in yellow, $Al_2O_3$ in blue, and Nafion in green), 12B (showing H-ZSM-5 in aquamarine, Nafion in orange, and A-36 in gray) and 12C (showing Nafion in blue and HZSM-5 in red). Although FIGS. 12A through 12C analyze the effects of catalyst selection on the conversion of nonanol to nonene (i.e.,

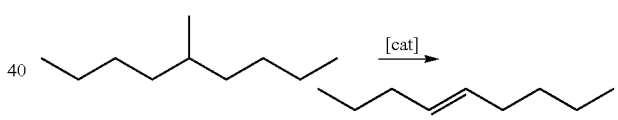

), the alcohols and ketones produced and reacted in the processes according to embodiments of the present invention react in much the same manner.

According to some embodiments, the processes and reactions described herein are conducted according to a batch reaction process. As would be understood by those of ordinary skill in the art, and as described herein, the batch reaction process involves reacting the reactants of the process in a closed vessel or batch reactor, and collecting the product in batches after the reactions are complete. Any suitable batch reactor and batch reaction process can be used, and those of ordinary skill in the art would be capable of selecting the appropriate equipment for such a batch process.

In some embodiments, however, the processes and reactions described herein may be conducted according to a continuous flow process. As would be understood by those of ordinary skill in the art, in a continuous flow protocol, the reactants are continuously fed into a reactor, and the product resulting from the reactions is output from the reactor as a continuous stream. Any suitable continuous flow reactor and protocol may be used, and those of ordinary skill in the art would be capable of selecting the appropriate equipment and protocol for such a continuous flow process. While either the batch process or continuous flow process may be used to form the alcohols and/or hydrocarbons according to embodiments of the present invention, the continuous flow process may be more desirable for large scale processing.

Additionally, both the batch and continuous flow processes may use the same reactants in the same proportions already described herein. Both the batch and continuous flow processes may also employ the same or similar reaction parameters, e.g., the same or similar temperatures and pressures. However, in some embodiments, the continuous flow process may employ a somewhat higher pressure. For example, in some embodiments, the continuous flow process may employ a pressure that is 50 to 150 psig higher than that of the batch process, for example 80 to 120 psig higher, or 100 psig higher. In some embodiments, for example, while the batch process may employ a reaction pressure of 100 to 350 psig (e.g., 200 to 300 psig), the continuous flow process may employ a reaction pressure of 150 to 500 psig (e.g., 250 to 450 psig), for example 180 to 470 psig (e.g., 280 to 420 psig), or 200 to 450 psig (e.g., 300 to 400 psig). Also, like the batch process, the reactant proportions and reaction parameters (e.g., temperature and/or pressure) in the continuous flow process may also be adjusted to tune the desired product outcome, as already described herein.

While certain exemplary embodiments of the present disclosure have been illustrated and described, those of ordinary skill in the art will recognize that various changes and modifications can be made to the described embodiments without departing from the spirit and scope of the present invention, and equivalents thereof, as defined in the claims that follow this description. For example, although certain components may have been described in the singular, i.e., "a" catalyst, and the like, one or more of these components in any combination can be used or produced according to the present disclosure.

Also, although certain embodiments have been described as "comprising" or "including" the specified components, embodiments "consisting essentially of" or "consisting of" the listed components are also within the scope of this disclosure. For example, while embodiments of the present invention are described as comprising condensing acetone and/or isopropanol to form one or more ketones, and hydrogenating and/or hydrodeoxygenating at least one of the one or more ketones, embodiments consisting essentially of or consisting of these actions are also within the scope of this disclosure. Accordingly, a process may consist essentially of condensing acetone and/or isopropanol to form one or more ketones, and hydrogenating and/or hydrodeoxygenating at least one or the one or more ketones. In this context, "consisting essentially of" means that any additional components or actions will not materially affect the chemical or physical properties of the resulting saturated or unsaturated hydrocarbons.

As used herein, unless otherwise expressly specified, all numbers such as those expressing values, ranges, amounts or percentages may be read as if prefaced by the word "about," even if the term does not expressly appear. Further, the word "about" is used as a term of approximation, and not as a term of degree, and reflects the penumbra of variation associated with measurement, significant figures, and interchangeability, all as understood by a person having ordinary skill in the art to which this disclosure pertains. Any numerical range recited herein is intended to include all sub-ranges subsumed therein. Plural encompasses singular and vice versa. For example, while the present disclosure may describe "a" catalyst, a mixture of such materials can be used. When ranges are given, any endpoints of those ranges and/or numbers within those ranges can be combined within the scope of the present disclosure. The terms "including" and like terms mean "including but not limited to," unless specified to the contrary.

Notwithstanding that the numerical ranges and parameters set forth herein may be approximations, numerical values set forth in the Examples are reported as precisely as is practical. Any numerical value, however, inherently contains certain errors necessarily resulting from the standard variation found in their respective testing measurements. The word "comprising" and variations thereof as used in this description and in the claims do not limit the disclosure to exclude any variants or additions.

What is claimed is:

1. A process for the production of a saturated or unsaturated aliphatic alcohol product and/or a saturated or unsaturated aliphatic hydrocarbon, the process comprising:
    condensing acetone and/or an alcohol reactant in the presence of first and second catalysts to form one or more carbonyl compounds, the first catalyst being different from the second catalyst, and the second catalyst being either unsupported or supported on a catalyst support, the catalyst support being different from the first catalyst, and the second catalyst comprising:
        a transition metal catalyst comprising a transition metal selected from the group consisting of Sc, Ti, V, Cr, Mn, Fe, Co, Ni, Cu, Zn and combinations thereof, or a zeolite catalyst;
    hydrogenating and/or hydrodeoxygenating at least one of the one or more carbonyl compounds to form the saturated or unsaturated alcohol product and/or the saturated or unsaturated hydrocarbon.

2. The process of claim 1, wherein the first catalyst comprises a solid acid or a base.

3. The process according to claim 2, wherein the first catalyst comprises an acidic cation exchange resin.

4. The process according to claim 1, wherein the second catalyst comprises Ni, Cu and/or Fe.

5. The process according to claim 1, wherein the second catalyst is supported on the catalyst support.

6. The process according to claim 5, wherein the catalyst support comprises carbon, alumina and/or silica.

7. The process according to claim 1, wherein the hydrogenating and/or hydrodeoxygenating the at least one of the one or more carbonyl compounds comprises:
    hydrogenating the at least one of the one or more carbonyl compounds to form one or more intermediate alcohols; and
    hydrodeoxygenating at least one of the one or more intermediate alcohols to form at least one saturated or unsaturated hydrocarbon.

8. The process according to claim 7, wherein the hydrogenating the at least one of the one or more carbonyl compounds is performed in the presence of a fourth catalyst.

9. The process according to claim 8, wherein the fourth catalyst comprises a transition metal catalyst, a zeolite catalyst, a precious metal catalyst, or a combination thereof.

10. The process according to claim 7, wherein the hydrodeoxygenating the at least one of the one or more intermediate alcohols is performed in the presence of a third catalyst.

11. The process according to claim 10, wherein the third catalyst comprises a solid acid or a base.

12. The process according to claim 1, wherein the hydrogenating and/or hydrodeoxygenating the at least one of the one or more carbonyl compounds comprises a one-pot process.

13. The process according to claim 12, wherein the one-pot process is performed in the presence of third and fourth catalysts.

14. The process according to claim 13, wherein the third catalyst comprises a solid acid or a base, and the fourth catalyst comprises a transition metal catalyst, a zeolite catalyst, a precious metal catalyst, or a combination thereof.

15. The process according to claim 1, wherein the one or more carbonyl compounds comprises one or more C6 carbonyl compounds, C9 carbonyl compounds and/or C12 carbonyl compounds.

16. The process according to claim 1, wherein the one or more carbonyl compounds comprises a mixture of at least two different carbonyl compounds.

17. The process according to claim 1, wherein the one or more carbonyl compounds comprises a mixture of 4-methyl-2-pentanone, 2,6-dimethyl-4-heptanone, 4,6-dimethyl-2-heptanone, and 2,6,8-trimethyl-4-nonanone.

18. The process according to claim 1, wherein the one or more carbonyl compounds comprises up to 36% carbon yield of 4-methyl-2-pentanone, up to 24% carbon yield of 2,6-dimethyl-4-heptanone, up to 6% carbon yield of 4,6-dimethyl-2-heptanone, and up to 34% carbon yield of 2,6,8-trimethyl-4-nonanone.

19. A process for the production of a saturated or unsaturated aliphatic alcohol product and/or a saturated or unsaturated aliphatic hydrocarbon, the process comprising:

converting an alcohol reactant to acetone;

condensing the acetone in the presence of first and second catalysts to form one or more carbonyl compounds, the first catalyst being different from the second catalyst, and the second catalyst being either unsupported or supported on a catalyst support, the catalyst support being different from the first catalyst, and the second catalyst comprising:

a transition metal catalyst comprising a transition metal selected from the group consisting of Sc, Ti, V, Cr, Mn, Fe, Co, Ni, Cu, Zn and combinations thereof, or a zeolite catalyst;

hydrogenating and/or hydrodeoxygenating at least one of the one or more carbonyl compounds to form the saturated or unsaturated alcohol product and/or the saturated or unsaturated hydrocarbon.

20. The process according to claim 19, wherein the converting the alcohol reactant to acetone is performed in the presence of a fifth catalyst comprising a transition metal catalyst, a zeolite catalyst, a precious metal catalyst, or a combination thereof.

* * * * *